(12) United States Patent
Lee et al.

(10) Patent No.: US 9,554,850 B2
(45) Date of Patent: *Jan. 31, 2017

(54) CATHETER DEVICE INCLUDING FLOW SENSING

(71) Applicant: MC10, Inc., Lexington, MA (US)

(72) Inventors: Stephen P. Lee, Cambridge, MA (US); Clifford Liu, Randolph, MA (US); Roozbeh Ghaffari, Cambridge, MA (US); John Work, South Dennis, MA (US); Fernando Quivira, Somerville, MA (US); Lauren E. Klinker, Cambridge, MA (US); Yung-Yu Hsu, Arlington, MA (US)

(73) Assignee: MC10, Inc., Lexington, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/874,148

(22) Filed: Oct. 2, 2015

(65) Prior Publication Data

US 2016/0095652 A1    Apr. 7, 2016

Related U.S. Application Data

(63) Continuation of application No. 13/844,677, filed on Mar. 15, 2013, now Pat. No. 9,168,094.

(Continued)

(51) Int. Cl.
*A61B 18/18* (2006.01)
*A61B 18/14* (2006.01)
(Continued)

(52) U.S. Cl.
CPC .......... *A61B 18/1492* (2013.01); *A61B 18/02* (2013.01); *A61B 18/18* (2013.01); *A61B 90/30* (2016.02);
(Continued)

(58) Field of Classification Search
CPC ....... A61B 5/4836; A61B 18/18; A61B 5/026; A61B 18/1492; A61B 18/02; A61N 1/32
See application file for complete search history.

(56) References Cited

U.S. PATENT DOCUMENTS

| 3,716,861 A | 2/1973 | Root |
| 3,805,427 A | 4/1974 | Epstein |

(Continued)

FOREIGN PATENT DOCUMENTS

| EP | 0585670 A2 | 3/1994 |
| EP | 2259062 A2 | 12/2010 |

(Continued)

OTHER PUBLICATIONS

Carvalhal et al., "Electrochemical Detection in a Paper-Based Separation Device", Analytical Chemistry, vol. 82, No. 3, (1162-1165) (4 pages) (Jan. 7, 2010).

(Continued)

*Primary Examiner* — Robert N Wieland
(74) *Attorney, Agent, or Firm* — Nixon Peabody LLP

(57) ABSTRACT

Devices and methods are provided for performing an ablation procedure on tissue with flow monitoring using flow sensors. The devices include a catheter, and at least one flow sensor disposed on the catheter, and a component for applying the ablation procedure. An assessment module provides an indication of the efficacy of the ablation procedure based on the flow measurement from the flow sensor.

42 Claims, 24 Drawing Sheets

Related U.S. Application Data

(60) Provisional application No. 61/733,575, filed on Dec. 5, 2012, provisional application No. 61/728,653, filed on Nov. 20, 2012, provisional application No. 61/668,338, filed on Jul. 5, 2012.

(51) Int. Cl.
| | |
|---|---|
| *A61B 18/02* | (2006.01) |
| *A61N 7/02* | (2006.01) |
| *A61B 18/22* | (2006.01) |
| *A61B 18/00* | (2006.01) |
| *A61N 1/05* | (2006.01) |
| *A61N 1/36* | (2006.01) |

(52) U.S. Cl.
CPC ............ *A61B 18/1815* (2013.01); *A61B 18/22* (2013.01); *A61B 2018/0022* (2013.01); *A61B 2018/00041* (2013.01); *A61B 2018/00178* (2013.01); *A61B 2018/00267* (2013.01); *A61B 2018/00273* (2013.01); *A61B 2018/00386* (2013.01); *A61B 2018/00404* (2013.01); *A61B 2018/00434* (2013.01); *A61B 2018/00511* (2013.01); *A61B 2018/00541* (2013.01); *A61B 2018/00577* (2013.01); *A61B 2018/00666* (2013.01); *A61B 2018/00702* (2013.01); *A61B 2018/00708* (2013.01); *A61B 2018/00791* (2013.01); *A61B 2018/00815* (2013.01); *A61B 2018/00821* (2013.01); *A61B 2018/00839* (2013.01); *A61B 2018/00863* (2013.01); *A61B 2018/0212* (2013.01); *A61B 2018/1861* (2013.01); *A61B 2090/065* (2016.02); *A61N 1/0551* (2013.01); *A61N 1/36017* (2013.01); *A61N 1/36117* (2013.01); *A61N 7/02* (2013.01)

(56) References Cited

U.S. PATENT DOCUMENTS

| | | |
|---|---|---|
| 4,304,235 A | 12/1981 | Kaufman |
| 4,416,288 A | 11/1983 | Freeman |
| 4,658,153 A | 4/1987 | Brosh |
| 5,306,917 A | 4/1994 | Black |
| 5,326,521 A | 7/1994 | East |
| 5,331,966 A | 7/1994 | Bennett |
| 5,360,987 A | 11/1994 | Shibib |
| 5,454,270 A | 10/1995 | Brown |
| 5,491,651 A | 2/1996 | Janic |
| 5,567,975 A | 10/1996 | Walsh |
| 5,580,794 A | 12/1996 | Allen |
| 5,617,870 A | 4/1997 | Hastings |
| 5,811,790 A | 9/1998 | Endo |
| 5,817,008 A | 10/1998 | Rafert |
| 5,907,477 A | 5/1999 | Tuttle |
| 6,063,046 A | 5/2000 | Allum |
| 6,282,960 B1 | 9/2001 | Samuels et al. |
| 6,343,514 B1 | 2/2002 | Smith |
| 6,387,052 B1 | 5/2002 | Quinn |
| 6,421,016 B1 | 7/2002 | Phillips |
| 6,567,158 B1 | 5/2003 | Falcial |
| 6,641,860 B1 | 11/2003 | Kaiserman |
| 6,775,906 B1 | 8/2004 | Silverbrook |
| 6,784,844 B1 | 8/2004 | Boakes |
| 6,965,160 B2 | 11/2005 | Cobbley |
| 6,987,314 B1 | 1/2006 | Yoshida |
| 7,259,030 B2 | 8/2007 | Daniels |
| 7,265,298 B2 | 9/2007 | Maghribi |
| 7,302,751 B2 | 12/2007 | Hamburgen |
| 7,337,012 B2 | 2/2008 | Maghribi |
| 7,487,587 B2 | 2/2009 | Vanfleteren |
| 7,491,892 B2 | 2/2009 | Wagner |
| 7,521,292 B2 | 4/2009 | Rogers |
| 7,557,367 B2 | 7/2009 | Rogers |
| 7,618,260 B2 | 11/2009 | Daniel |
| 7,622,367 B1 | 11/2009 | Nuzzo |
| 7,727,228 B2 | 6/2010 | Abboud |
| 7,739,791 B2 | 6/2010 | Brandenburg |
| 7,759,167 B2 | 7/2010 | Vanfleteren |
| 7,960,246 B2 | 6/2011 | Flamand |
| 7,982,296 B2 | 7/2011 | Nuzzo |
| 8,097,926 B2 | 1/2012 | De Graff |
| 8,198,621 B2 | 6/2012 | Rogers |
| 8,207,473 B2 | 6/2012 | Axisa |
| 8,217,381 B2 | 7/2012 | Rogers |
| 8,372,726 B2 | 2/2013 | De Graff |
| 8,389,862 B2 | 3/2013 | Arora |
| 8,431,828 B2 | 4/2013 | Vanfleteren |
| 8,440,546 B2 | 5/2013 | Nuzzo |
| 8,536,667 B2 | 9/2013 | De Graff |
| 8,552,299 B2 | 10/2013 | Rogers |
| 8,664,699 B2 | 3/2014 | Nuzzo |
| 8,679,888 B2 | 3/2014 | Rogers |
| 8,729,524 B2 | 5/2014 | Rogers |
| 8,754,396 B2 | 6/2014 | Rogers |
| 8,865,489 B2 | 10/2014 | Rogers |
| 8,886,334 B2 | 11/2014 | Ghaffari |
| 8,905,772 B2 | 12/2014 | Rogers |
| 9,012,784 B2 | 4/2015 | Arora |
| 9,082,025 B2 | 7/2015 | Fastert |
| 9,105,555 B2 | 8/2015 | Rogers |
| 9,105,782 B2 | 8/2015 | Rogers |
| 9,119,533 B2 | 9/2015 | Ghaffari |
| 9,123,614 B2 | 9/2015 | Graff |
| 9,159,635 B2 | 10/2015 | Elolampi |
| 9,168,094 B2 | 10/2015 | Lee |
| 9,171,794 B2 | 10/2015 | Rafferty |
| 9,186,060 B2 | 11/2015 | De Graff |
| 9,226,402 B2 | 12/2015 | Hsu |
| 2001/0012918 A1 | 8/2001 | Swanson |
| 2001/0021867 A1 | 9/2001 | Kordis |
| 2002/0026127 A1 | 2/2002 | Balbierz |
| 2002/0082515 A1 | 6/2002 | Campbell |
| 2002/0094701 A1 | 7/2002 | Biegelsen |
| 2002/0113739 A1 | 8/2002 | Howard |
| 2002/0128700 A1 | 9/2002 | Cross, Jr. |
| 2002/0145467 A1 | 10/2002 | Minch |
| 2002/0151934 A1 | 10/2002 | Levine |
| 2002/0158330 A1 | 10/2002 | Moon |
| 2003/0017848 A1 | 1/2003 | Engstrom |
| 2003/0045025 A1 | 3/2003 | Coyle |
| 2003/0097165 A1 | 5/2003 | Krulevitch |
| 2003/0120271 A1 | 6/2003 | Burnside |
| 2003/0162507 A1 | 8/2003 | Vatt |
| 2003/0214408 A1 | 11/2003 | Grajales |
| 2003/0236455 A1 | 12/2003 | Swanson |
| 2004/0006264 A1 | 1/2004 | Mojarradi |
| 2004/0085469 A1 | 5/2004 | Johnson |
| 2004/0092806 A1 | 5/2004 | Sagon |
| 2004/0106334 A1 | 6/2004 | Suzuki |
| 2004/0135094 A1 | 7/2004 | Niigaki |
| 2004/0138558 A1 | 7/2004 | Dunki-Jacobs |
| 2004/0149921 A1 | 8/2004 | Smyk |
| 2004/0178466 A1 | 9/2004 | Merrill |
| 2004/0192082 A1 | 9/2004 | Wagner |
| 2004/0201134 A1 | 10/2004 | Kawai |
| 2004/0203486 A1 | 10/2004 | Shepherd |
| 2004/0221370 A1 | 11/2004 | Hannula |
| 2004/0243204 A1 | 12/2004 | Maghribi |
| 2005/0021103 A1 | 1/2005 | DiLorenzo |
| 2005/0067293 A1 | 3/2005 | Naito |
| 2005/0070778 A1 | 3/2005 | Lackey |
| 2005/0096513 A1 | 5/2005 | Ozguz |
| 2005/0113744 A1 | 5/2005 | Donoghue |
| 2005/0139683 A1 | 6/2005 | Yi |
| 2005/0171524 A1 | 8/2005 | Stern |
| 2005/0203366 A1 | 9/2005 | Donoghue |
| 2006/0003709 A1 | 1/2006 | Wood |
| 2006/0038182 A1 | 2/2006 | Rogers |
| 2006/0071349 A1 | 4/2006 | Tokushige |
| 2006/0084394 A1 | 4/2006 | Engstrom |
| 2006/0106321 A1 | 5/2006 | Lewinsky |
| 2006/0128346 A1 | 6/2006 | Yasui |

(56) References Cited

U.S. PATENT DOCUMENTS

| | | |
|---|---|---|
| 2006/0154398 A1 | 7/2006 | Qing |
| 2006/0160560 A1 | 7/2006 | Josenhans |
| 2006/0235314 A1* | 10/2006 | Migliuolo ............ A61B 1/0011 600/505 |
| 2006/0248946 A1 | 11/2006 | Howell |
| 2006/0257945 A1 | 11/2006 | Masters |
| 2006/0264767 A1 | 11/2006 | Shennib |
| 2006/0286785 A1 | 12/2006 | Rogers |
| 2007/0027514 A1 | 2/2007 | Gerber |
| 2007/0031283 A1 | 2/2007 | Davis |
| 2007/0108389 A1 | 5/2007 | Makela |
| 2007/0113399 A1 | 5/2007 | Kumar |
| 2007/0123756 A1 | 5/2007 | Kitajima |
| 2007/0270672 A1 | 11/2007 | Hayter |
| 2008/0046080 A1 | 2/2008 | Vanden Bulcke |
| 2008/0074383 A1 | 3/2008 | Dean |
| 2008/0096620 A1 | 4/2008 | Lee |
| 2008/0139894 A1 | 6/2008 | Szydlo-Moore |
| 2008/0157235 A1 | 7/2008 | Rogers |
| 2008/0193749 A1 | 8/2008 | Thompson |
| 2008/0204021 A1 | 8/2008 | Leussler |
| 2008/0211087 A1 | 9/2008 | Mueller-Hipper |
| 2008/0237840 A1 | 10/2008 | Alcoe |
| 2008/0259576 A1 | 10/2008 | Johnson |
| 2008/0287167 A1 | 11/2008 | Caine |
| 2008/0313552 A1 | 12/2008 | Buehler |
| 2009/0000377 A1 | 1/2009 | Shipps |
| 2009/0001550 A1 | 1/2009 | Li et al. |
| 2009/0015560 A1 | 1/2009 | Robinson |
| 2009/0017884 A1 | 1/2009 | Rotschild |
| 2009/0024016 A1 | 1/2009 | Zhang |
| 2009/0048556 A1 | 2/2009 | Durand |
| 2009/0088750 A1 | 4/2009 | Hushka |
| 2009/0107704 A1 | 4/2009 | Vanfleteren |
| 2009/0154736 A1 | 6/2009 | Lee |
| 2009/0184254 A1 | 7/2009 | Miura |
| 2009/0204168 A1 | 8/2009 | Kallmeyer |
| 2009/0215385 A1 | 8/2009 | Waters |
| 2009/0225751 A1 | 9/2009 | Koenck |
| 2009/0261828 A1 | 10/2009 | Nordmeyer-Massner |
| 2009/0273909 A1 | 11/2009 | Shin |
| 2009/0291508 A1 | 11/2009 | Babu |
| 2009/0294803 A1 | 12/2009 | Nuzzo |
| 2009/0322480 A1 | 12/2009 | Benedict |
| 2010/0002402 A1 | 1/2010 | Rogers |
| 2010/0059863 A1 | 3/2010 | Rogers |
| 2010/0072577 A1 | 3/2010 | Nuzzo |
| 2010/0073669 A1 | 3/2010 | Colvin |
| 2010/0087782 A1 | 4/2010 | Ghaffari |
| 2010/0090781 A1 | 4/2010 | Yamamoto |
| 2010/0090824 A1 | 4/2010 | Rowell |
| 2010/0116526 A1 | 5/2010 | Arora |
| 2010/0117660 A1 | 5/2010 | Douglas |
| 2010/0178722 A1 | 7/2010 | De Graff |
| 2010/0245011 A1 | 9/2010 | Chatzopoulos |
| 2010/0271191 A1 | 10/2010 | De Graff |
| 2010/0298895 A1 | 11/2010 | Ghaffari |
| 2010/0317132 A1 | 12/2010 | Rogers |
| 2010/0321161 A1 | 12/2010 | Isabell |
| 2010/0327387 A1 | 12/2010 | Kasai |
| 2011/0011179 A1 | 1/2011 | Gustafsson |
| 2011/0034912 A1 | 2/2011 | De Graff |
| 2011/0051384 A1 | 3/2011 | Kriechbaum |
| 2011/0054583 A1 | 3/2011 | Litt |
| 2011/0101789 A1 | 5/2011 | Salter |
| 2011/0121822 A1 | 5/2011 | Parsche |
| 2011/0140897 A1 | 6/2011 | Purks |
| 2011/0175735 A1 | 7/2011 | Forster |
| 2011/0184320 A1 | 7/2011 | Shipps |
| 2011/0215931 A1 | 9/2011 | Callsen |
| 2011/0218756 A1 | 9/2011 | Callsen |
| 2011/0218757 A1 | 9/2011 | Callsen |
| 2011/0220890 A1 | 9/2011 | Nuzzo |
| 2011/0277813 A1 | 11/2011 | Rogers |
| 2011/0306851 A1 | 12/2011 | Wang |
| 2012/0016258 A1 | 1/2012 | Webster |
| 2012/0051005 A1 | 3/2012 | Vanfleteren |
| 2012/0052268 A1 | 3/2012 | Axisa |
| 2012/0065937 A1 | 3/2012 | De Graff |
| 2012/0071870 A1 | 3/2012 | Salahieh |
| 2012/0074546 A1 | 3/2012 | Chong |
| 2012/0087216 A1 | 4/2012 | Keung |
| 2012/0091594 A1 | 4/2012 | Landesberger |
| 2012/0092178 A1 | 4/2012 | Callsen |
| 2012/0092222 A1 | 4/2012 | Kato |
| 2012/0101413 A1 | 4/2012 | Beetel |
| 2012/0101538 A1 | 4/2012 | Ballakur |
| 2012/0108012 A1 | 5/2012 | Yasuda |
| 2012/0136350 A1* | 5/2012 | Goshgarian ........ A61B 18/1492 606/41 |
| 2012/0143293 A1 | 6/2012 | Mauch |
| 2012/0157804 A1 | 6/2012 | Rogers |
| 2012/0172697 A1 | 7/2012 | Urman |
| 2012/0226130 A1 | 9/2012 | De Graff |
| 2012/0244848 A1 | 9/2012 | Ghaffari |
| 2012/0256308 A1 | 10/2012 | Helin |
| 2012/0316455 A1 | 12/2012 | Rahman |
| 2012/0327608 A1 | 12/2012 | Rogers |
| 2013/0041235 A1 | 2/2013 | Rogers |
| 2013/0099358 A1 | 4/2013 | Elolampi |
| 2013/0100618 A1 | 4/2013 | Rogers |
| 2013/0118255 A1 | 5/2013 | Callsen |
| 2013/0150693 A1 | 6/2013 | D'angelo |
| 2013/0185003 A1 | 7/2013 | Carbeck |
| 2013/0192356 A1 | 8/2013 | De Graff |
| 2013/0200268 A1 | 8/2013 | Rafferty |
| 2013/0211761 A1 | 8/2013 | Brandsma |
| 2013/0214300 A1 | 8/2013 | Lerman |
| 2013/0215467 A1 | 8/2013 | Fein |
| 2013/0225965 A1 | 8/2013 | Ghaffari |
| 2013/0237150 A1 | 9/2013 | Royston |
| 2013/0245388 A1 | 9/2013 | Rafferty |
| 2013/0274562 A1 | 10/2013 | Ghaffari |
| 2013/0313713 A1 | 11/2013 | Arora |
| 2013/0316442 A1 | 11/2013 | Meurville |
| 2013/0316487 A1 | 11/2013 | De Graff |
| 2013/0320503 A1 | 12/2013 | Nuzzo |
| 2013/0321373 A1 | 12/2013 | Yoshizumi |
| 2014/0001058 A1 | 1/2014 | Ghaffari |
| 2014/0012160 A1 | 1/2014 | Ghaffari |
| 2014/0012242 A1 | 1/2014 | Lee |
| 2014/0022746 A1 | 1/2014 | Hsu |
| 2014/0039290 A1 | 2/2014 | De Graff |
| 2014/0097944 A1 | 4/2014 | Fastert |
| 2014/0110859 A1 | 4/2014 | Rafferty |
| 2014/0114305 A1 | 4/2014 | Zarins |
| 2014/0140020 A1 | 5/2014 | Rogers |
| 2014/0188426 A1 | 7/2014 | Fastert |
| 2014/0191236 A1 | 7/2014 | Nuzzo |
| 2014/0216524 A1 | 8/2014 | Rogers |
| 2014/0240932 A1 | 8/2014 | Hsu |
| 2014/0249520 A1 | 9/2014 | Ghaffari |
| 2014/0303452 A1 | 10/2014 | Ghaffari |
| 2014/0340857 A1 | 11/2014 | Hsu |
| 2014/0374872 A1 | 12/2014 | Rogers |
| 2014/0375465 A1 | 12/2014 | Fenuccio |
| 2015/0001462 A1 | 1/2015 | Rogers |
| 2015/0019135 A1 | 1/2015 | Kacyvenski |
| 2015/0035680 A1 | 2/2015 | Li |
| 2015/0069617 A1 | 3/2015 | Arora |
| 2015/0099976 A1 | 4/2015 | Ghaffari |
| 2015/0100135 A1 | 4/2015 | Ives |
| 2015/0173673 A1* | 6/2015 | Toth .................... A61B 5/4839 600/301 |
| 2015/0194817 A1 | 7/2015 | Lee |
| 2015/0237711 A1 | 8/2015 | Rogers |
| 2015/0241288 A1 | 8/2015 | Keen |
| 2015/0260713 A1 | 9/2015 | Ghaffari |
| 2015/0272652 A1 | 10/2015 | Ghaffari |
| 2015/0286913 A1 | 10/2015 | Fastert |
| 2015/0320472 A1 | 11/2015 | Ghaffari |

(56) References Cited

U.S. PATENT DOCUMENTS

| | | |
|---|---|---|
| 2015/0335254 A1 | 11/2015 | Fastert |
| 2015/0342036 A1 | 11/2015 | Elolampi |

FOREIGN PATENT DOCUMENTS

| | | |
|---|---|---|
| JP | 05-087511 A | 4/1993 |
| JP | 2009-170173 A | 7/2009 |
| WO | WO 99/38211 A2 | 7/1999 |
| WO | WO 03/021679 A2 | 3/2003 |
| WO | WO 2005/122285 A2 | 12/2005 |
| WO | WO 2007/003019 A2 | 1/2007 |
| WO | WO 2007/116344 A1 | 10/2007 |
| WO | WO 2007/136726 A2 | 11/2007 |
| WO | WO 2008/030960 A2 | 3/2008 |
| WO | WO 2009/111641 A1 | 9/2009 |
| WO | WO 2009/114689 A1 | 9/2009 |
| WO | WO 2010/036807 A1 | 4/2010 |
| WO | WO 2010/042653 A1 | 4/2010 |
| WO | WO 2010/042957 A2 | 4/2010 |
| WO | WO 2010/046883 A1 | 4/2010 |
| WO | WO 2010/056857 A2 | 5/2010 |
| WO | WO 2010/081137 A2 | 7/2010 |
| WO | WO 2010/082993 A2 | 7/2010 |
| WO | WO 2010/102310 A2 | 9/2010 |
| WO | WO 2010/132552 A1 | 11/2010 |
| WO | WO 2011/003181 A1 | 1/2011 |
| WO | WO 2011/041727 A1 | 4/2011 |
| WO | WO 2011/084450 A1 | 7/2011 |
| WO | WO 2011/084709 A2 | 7/2011 |
| WO | WO 2011/127331 A2 | 10/2011 |
| WO | WO 2012/125494 A2 | 9/2012 |
| WO | WO 2012/166686 A2 | 12/2012 |
| WO | WO 2013/010171 A1 | 1/2013 |
| WO | WO 2013/022853 A1 | 2/2013 |
| WO | WO 2013/033724 A1 | 3/2013 |
| WO | WO 2013/034987 A3 | 3/2013 |
| WO | WO 2013/049716 A1 | 4/2013 |
| WO | WO 2013/052919 A2 | 4/2013 |
| WO | WO 2013/170032 A2 | 11/2013 |
| WO | WO 2014/007871 A1 | 1/2014 |
| WO | WO 2014/058473 A1 | 4/2014 |
| WO | WO 2014/059032 A1 | 4/2014 |
| WO | WO 2014/106041 A1 | 7/2014 |
| WO | WO 2014/110176 A1 | 7/2014 |
| WO | WO 2014/130928 A2 | 8/2014 |
| WO | WO 2014/130931 A1 | 8/2014 |
| WO | WO 2014/186467 A2 | 11/2014 |
| WO | WO 2014/197443 A1 | 12/2014 |
| WO | WO 2014/205434 A2 | 12/2014 |
| WO | WO 2015/021039 A1 | 2/2015 |
| WO | WO 2015/054312 A1 | 4/2015 |
| WO | WO 2015/077559 A1 | 5/2015 |
| WO | WO 2015/080991 A1 | 6/2015 |
| WO | WO 2015/102951 A2 | 7/2015 |
| WO | WO 2015/103483 A1 | 7/2015 |
| WO | WO 2015/103580 A2 | 7/2015 |
| WO | WO 2015/127458 A1 | 8/2015 |
| WO | WO 2015/134588 A1 | 9/2015 |
| WO | WO 2015/138712 A1 | 9/2015 |

OTHER PUBLICATIONS

Demura et al., "Immobilization of Glucose Oxidase with *Bombyx mori* Silk Fibroin by Only Stretching Treatment and its Application to Glucose Sensor," Biotechnology and Bioengineering, vol. 33, 598-603 (6 pages) (1989).

Ellerbee et al., "Quantifying Colorimetric Assays in Paper-Based Microfluidic Devices by Measuring the Transmission of Light through Paper," Analytical Chemistry, vol. 81, No. 20 8447-8452, (6 pages) (Oct. 15, 2009).

Halsted, "Ligature and Suture Material," Journal of the American Medical Association, vol. LX, No. 15, 1119-1126, (8 pages) (Apr. 12, 1913).

Kim et al., "Complementary Metal Oxide Silicon Integrated Circuits Incorporating Monolithically Integrated Stretchable Wavy Interconnects," Applied Physics Letters, vol. 93, 044102-044102.3 (3 pages) (Jul. 31, 2008).

Kim et al., "Dissolvable Films of Silk Fibroin for Ultrathin Conformal Bio-Integrated Electronics," Nature, 1-8 (8 pages) (Apr. 18, 2010).

Kim et al., "Materials and Noncoplanar Mesh Designs for Integrated Circuits with Linear Elastic Responses to Extreme Mechanical Deformations," PNAS, vol. 105, No. 48, 18675-18680 (6 pages) (Dec. 2, 2008).

Kim et al., "Stretchable and Foldable Silicon Integrated Circuits," Science, vol. 320, 507-511 (5 pages) (Apr. 25, 2008).

Kim et al., "Electrowetting on Paper for Electronic Paper Display," ACS Applied Materials & Interfaces, vol. 2, No. 11, (3318-3323) (6 pages) (Nov. 24, 2010).

Ko et al., "A Hemispherical Electronic Eye Camera Based on Compressible Silicon Optoelectronics," Nature, vol. 454, 748-753 (6 pages) (Aug. 7, 2008).

Lawrence et al., "Bioactive Silk Protein Biomaterial Systems for Optical Devices," Biomacromolecules, vol. 9, 1214-1220 (7 pages) (Nov. 4, 2008).

Meitl et al., "Transfer Printing by Kinetic Control of Adhesion to an Elastomeric Stamp," Nature, vol. 5, 33-38 (6 pages) (Jan. 2006).

Omenetto et al., "A New Route for Silk," Nature Photonics, vol. 2, 641-643 (3 pages) (Nov. 2008).

Omenetto et al., "New Opportunities for an Ancient Material," Science, vol. 329, 528-531 (5 pages) (Jul. 30, 2010).

Siegel et al., "Foldable Printed Circuit Boards on Paper Substrates," Advanced Functional Materials, vol. 20, No. 1, 28-35, (8 pages) (Jan. 8, 2010).

Tsukada et al., "Structural Changes of Silk Fibroin Membranes Induced by Immersion in Methanol Aqueous Solutions," Journal of Polymer Science, vol. 32, 961-968 (8 pages) (1994).

Wang et al., "Controlled Release From Multilayer Silk Biomaterial Coatings to Modulate Vascular Cell Responses" Biomaterials, 29, 894-903 (10 pages) (Nov. 28, 2008).

Non-final Office Action for U.S. Appl. No. 14/147,347 dated Jul. 27, 2015, (19 pages).

International Search Report for International Application No. PCT/US13/32714 dated Jun. 5, 2013, (2 pages).

Written Opinion for International Application No. PCT/US13/32714 dated Jun. 5, 2013, (11 pages).

International Search Report for International Application No. PCT/US2014/071516 dated Jun. 4, 2015, (4 pages).

Written Opinion for International Application No. PCT/US2014/071516 dated Jun. 4, 2015, (9 pages).

\* cited by examiner

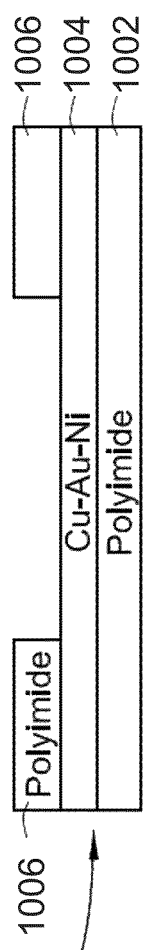
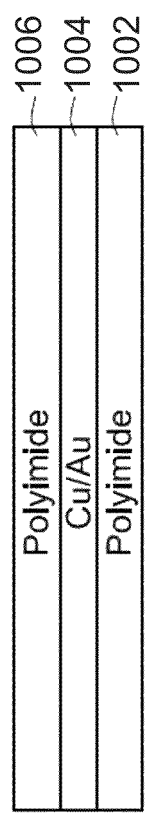
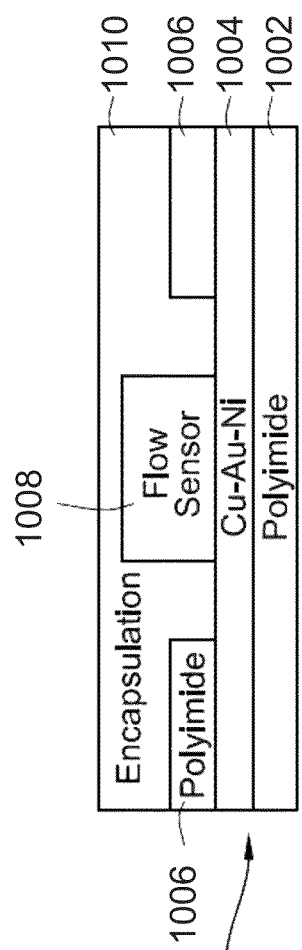
FIG. 10A
FIG. 10B
FIG. 10C

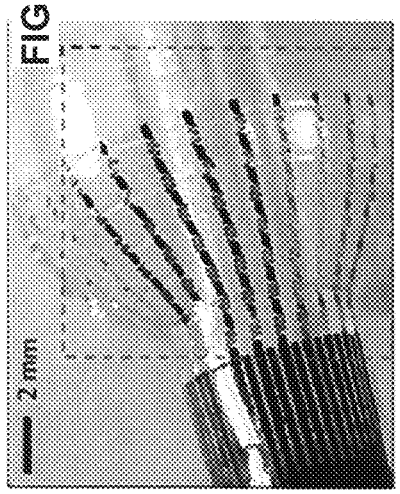
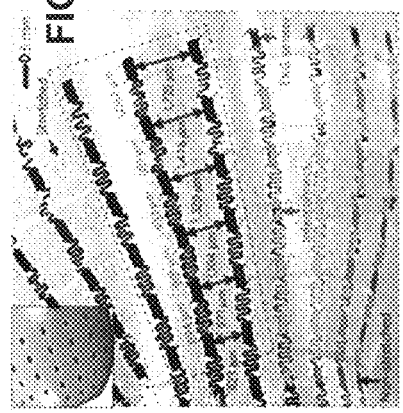
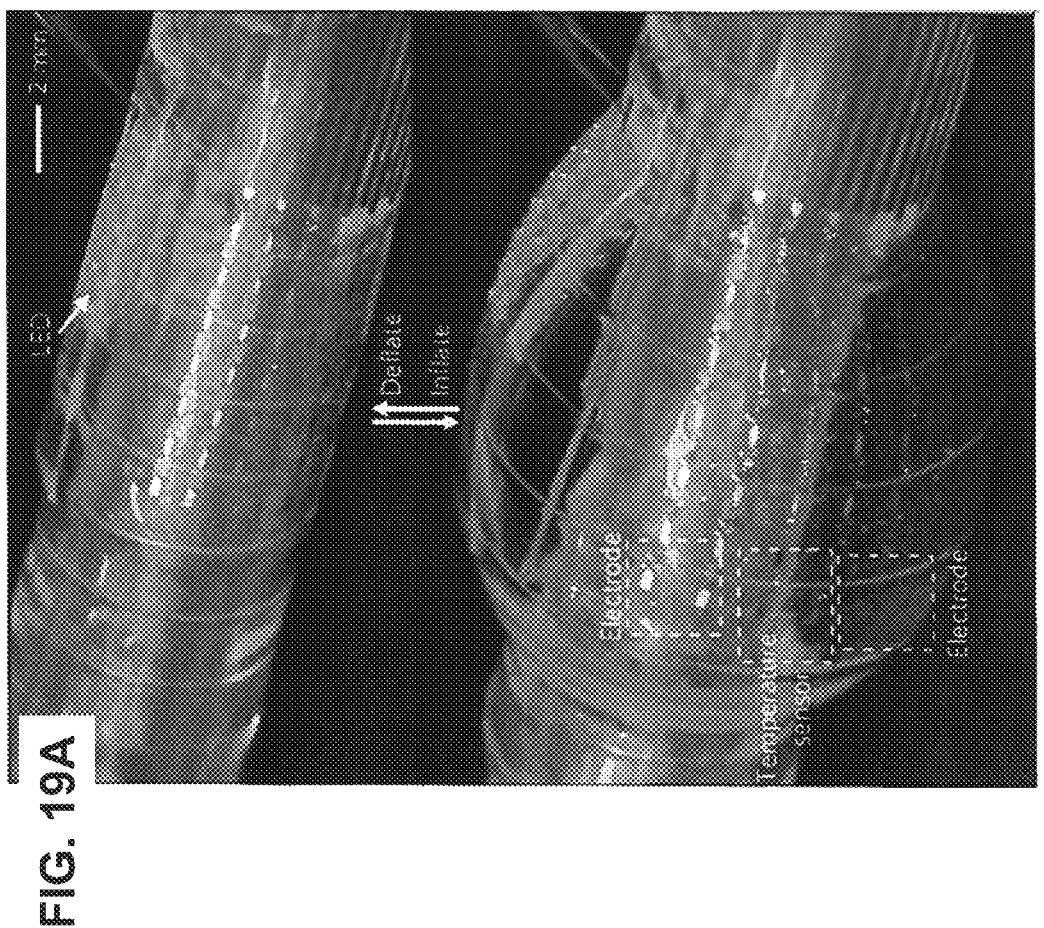

CATHETER DEVICE INCLUDING FLOW SENSING

CROSS-REFERENCE TO RELATED APPLICATIONS

This application is a continuation of U.S. application Ser. No. 13/844,677, filed on Mar. 15, 2013, entitled "CATHETER DEVICE INCLUDING FLOW SENSING," now U.S. Pat. No. 9,168,094, issued Oct. 27, 2015, which claims priority to U.S. Provisional Application No. 61/668,338, filed on Jul. 5, 2012, entitled "METHOD AND APPARATUS FOR DENERVATION," U.S. Provisional Application No. 61/728,653, filed on Nov. 20, 2012, entitled "RENAL DENERVATION," and U.S. Provisional Application No. 61/733,575, filed on Dec. 5, 2012, entitled "INCREASING THE RESOLUTION OF TEMPERATURE MEASUREMENT FOR FLOW DETECTION IN THE RENAL ARTERY," each of which is hereby incorporated herein by reference in its entirety, including drawings.

BACKGROUND

Diseases such as heart disease, stroke and hypertension are a global epidemics that affects billions of people worldwide Hypertension underlies the progression of several debilitating diseases, including heart disease and stroke. Despite widespread use of anti-hypertension medication to counter high blood pressure, the prevalence of hypertension is alarmingly high and constitutes a severe economic burden on health care.

Blood pressure is controlled, in large part, by the sympathetic nervous system. The sympathetic nervous system involves several organs that are responsible for regulating blood pressure such as the brain, heart and kidneys. The kidney is a key element in long-term blood pressure regulation. Hypertension, or high blood pressure, results from hyperactive renal nerves. This, in turn, can cause heart, kidney, and blood vessel damage.

SUMMARY

The Inventors have recognized that an ability to monitor procedures during treatment of tissue is advantageous. For example, renal ablation represents a useful and potentially safe technique. Its applicability may be limited due to a lack of sensing capability following ablation.

In view of the foregoing, various examples described herein are directed generally to systems, apparatus and methods for facilitating the verification verifying the outcome of renal nerve denervation, which can be used to determine a clinical endpoint of a denervatin procedure. Systems and methods described herein also facilitate establishing a credible endpoint in renal sympathetic denervation procedures.

Systems and methods described herein provide novel devices, including catheter devices, with diagnostic capabilities, to assess the state of the renal arteries following each procedure, including each ablation cycle of a series of ablation cycles.

Systems and methods described herein provide novel devices, including catheter devices, with diagnostic capabilities, to assess the state of the tissue in other systems, including in pulmonary veins, coronary arteries, and peripheral blood vessels, following each procedure in a series of procedures, such as each ablation cycle of a series of ablation cycles.

In an example, a system, apparatus and method is provided that is based on thin device islands, including integrated circuitry (IC) chips and/or stretchable and/or flexible interconnects that are encapsulated in an encapsulant.

In an example, a system, apparatus and method is provided that includes a catheter, at least one flow sensor coupled to the catheter; at least one component coupled to the catheter to perform an ablation procedure on a portion of a tissue proximate to the catheter, and an assessment module coupled to the flow sensor to receive data indicative of at least one flow measurement from the at least one flow sensor and provide an indication of the efficacy of the ablation procedure based on the data indicative of at least one flow measurement.

In an example, a system, apparatus and method can further include an inflatable and/or expandable body coupled to the catheter, and an electronic circuit disposed on the inflatable and/or expandable body, the electronic circuit includes a plurality of components that accommodate expanding of the inflatable and/or expandable body, the plurality of components including a plurality of electrodes, at least one electrode of the plurality of electrodes is a radiofrequency electrode to deliver a radiofrequency energy to a tissue proximate to the radiofrequency electrode.

The tissue proximate the catheter can be a portion of a renal artery and where the measurement of the flow sensor provides an indication of a rate of renal blood flow.

The can further include an electronic circuit disposed on the catheter, the electronic circuit includes a plurality of electrodes, where at least one electrode of the plurality of electrodes is a pacing electrode to deliver an electrical stimulation to a portion of the renal artery proximate to the pacing electrode.

The electrical stimulation can be applied to the portion of the renal artery prior to performance of the ablation procedure on the portion of the renal artery.

In an example, the electrical stimulation is applied to the portion of the renal artery subsequent performance of the ablation procedure on the portion of the renal artery.

In an example, the temperature sensor can be a thermistor, a thermocouple, a resistance temperature detector, a junction potential temperature sensor, an integrated-circuit temperature sensor, or a semiconductor temperature sensor.

The ablation procedure can be a radiofrequency ablation, a cryo-ablation, an ultrasound ablation, a laser-light-based ablation, a drug-based ablation, an ultrasound energy ablation, an alcohol injection-based ablation, or a microwave energy ablation.

In an example, the device can further include an electronic circuit disposed on the catheter, the electronic circuit includes at least one radiofrequency electrode, where the at least one radiofrequency electrode is a bipolar electrode or a unipolar electrode.

In an example, the device can further include an electronic circuit disposed on the catheter, the electronic circuit includes a plurality of components, where the plurality of components further comprises at least one of a light-emitting device, a contact sensor, an image detector, a mapping electrode, a pressure sensor, a biological activity sensors, and a temperature sensor.

The device can also include an inflatable and/or expandable body coupled to the catheter, where the inflatable and/or expandable body is a compliant balloon or a non-compliant balloon.

The device can further includes an inflatable and/or expandable body coupled to the catheter, where the inflatable and/or expandable body is an expandable spiral coil, an expandable mesh, or a deployable netting.

In an example, the device can further include an inflatable and/or expandable body coupled to the catheter, an electronic circuit disposed on the inflatable and/or expandable body, the electronic circuit includes a plurality of components, and at least four flow sensors disposed on the portion of the inflatable and/or expandable body, and where the plurality of components comprises at least four pacing electrodes and at least four radiofrequency electrodes.

In an example, the tissue is a portion of a tissue lumen.

The tissue can be a renal artery, a pulmonary vein, a coronary artery, or a peripheral blood vessel.

In an example, a system, apparatus and method is provided for performing a medical diagnosis and/or treatment on a tissue. The method includes disposing in proximity to the tissue. The apparatus includes a catheter, at least one flow sensor disposed on a portion of the catheter, each of the at least one flow sensor including a heating element, and a temperature sensor disposed proximate to the heating element, and an assessment module coupled to the flow sensor to receive data indicative of at least one flow measurement from the at least one flow sensor and provide an indication of the efficacy of the ablation procedure based on the data indicative of at least one flow measurement. A flow measurement of the flow sensor can be used to provide an indication of a flow rate of a fluid proximate to the inflatable and/or expandable body. At least one component coupled to the catheter to perform an ablation procedure on a portion of a tissue proximate to the catheter. The method can further include applying the ablation procedure to the surface of the tissue proximate to the catheter, and recording the flow measurement of the flow sensor, where the assessment module provides the indication of the efficacy of the ablation procedure.

In an example, a system, apparatus and method is provided for recording the flow measurement prior to and subsequent to performing the ablation procedure, where the ablation procedure is a radiofrequency ablation, a cryo-ablation, an ultrasound ablation, a laser-light-based ablation, a drug-based ablation, an ultrasound energy ablation, an alcohol injection-based ablation, or a microwave energy ablation of the tissue.

In an example, a system, apparatus and method is provided for recording of the flow measurement of the flow sensor is performed subsequent to the applying of the ablation procedure to the surface of the tissue proximate to the catheter.

In an example, a system, apparatus and method is provided for recording of the flow measurement of the flow sensor is performed prior to the applying of the ablation procedure to the surface of the tissue proximate to the catheter.

The example, a system, apparatus and method can further include recording of the flow measurement of the flow sensor subsequent to the applying of the ablation procedure to the surface of the tissue proximate to the catheter, and comparing data indicative of the flow measurement prior to the applying of the ablation procedure to data indicative of the flow measurement subsequent to the applying of the ablation procedure to provide the indication of the efficacy of the ablation procedure.

In an example system, apparatus and method provided herein, an indication of an increase in the flow rate of the fluid provides an indication of the efficacy of the applying of the ablation procedure to the surface of the tissue.

The catheter can further include a pacing electrode to deliver an electrical stimulation to a portion of the tissue proximate to the pacing electrode.

The method can further include delivering the electrical stimulation to the portion of the tissue proximate to the pacing electrode prior to the recording of the temperature measurement of the temperature sensor.

The tissue can be a left renal artery, a right renal artery, and/or a carotid body.

an example system, apparatus and method provided herein, an indication of an increase in the flow rate of the fluid provides an indication of the efficacy of the applying of the ablation procedure to the surface of the left renal artery, the right renal artery, and/or the carotid body.

An example system, apparatus and method herein provides a catheter device for performing a procedure on tissue of a renal artery. The catheter device includes an inflatable and/or expandable body disposed near a distal end of the catheter, at least one flow sensor disposed on the inflatable and/or expandable body. At least one component coupled to the catheter to perform an ablation procedure on a portion of the tissue of the renal artery. Each of the at least one flow sensor includes a heating element to heat an area proximate to the inflatable and/or expandable body, and a temperature sensor disposed proximate to the heating element, where measurement of the temperature sensor provides an indication of a flow rate of blood in the renal artery proximate to the inflatable and/or expandable body.

The following publications, patents, and patent applications are hereby incorporated herein by reference in their entirety:

Kim et al., "Stretchable and Foldable Silicon Integrated Circuits," Science Express, Mar. 27, 2008, 10.1126/science.1154367;

Ko et al., "A Hemispherical Electronic Eye Camera Based on Compressible Silicon Optoelectronics," Nature, Aug. 7, 2008, vol. 454, pp. 748-753;

Kim et al., "Complementary Metal Oxide Silicon Integrated Circuits Incorporating Monolithically Integrated Stretchable Wavy Interconnects," Applied Physics Letters, Jul. 31, 2008, vol. 93, 044102;

Kim et al., "Materials and Noncoplanar Mesh Designs for Integrated Circuits with Linear Elastic Responses to Extreme Mechanical Deformations," PNAS, Dec. 2, 2008, vol. 105, no. 48, pp. 18675-18680;

Meitl et al., "Transfer Printing by Kinetic Control of Adhesion to an Elastomeric Stamp," Nature Materials, January, 2006, vol. 5, pp. 33-38;

U.S. Patent Application publication no. 2010 0002402-A1, published Jan. 7, 2010, filed Mar. 5, 2009, and entitled "STRETCHABLE AND FOLDABLE ELECTRONIC DEVICES;"

U.S. Patent Application publication no. 2010 0087782-A1, published Apr. 8, 2010, filed Oct. 7, 2009, and entitled "CATHETER BALLOON HAVING STRETCHABLE INTEGRATED CIRCUITRY AND SENSOR ARRAY;"

U.S. Patent Application publication no. 2010 0116526-A1, published May 13, 2010, filed Nov. 12, 2009, and entitled "EXTREMELY STRETCHABLE ELECTRONICS;"

U.S. Patent Application publication no. 2010 0178722-A1, published Jul. 15, 2010, filed Jan. 12, 2010, and entitled "METHODS AND APPLICATIONS OF NON-PLANAR IMAGING ARRAYS;" and U.S. Patent Application publication no. 2010 027119-A1, published Oct. 28, 2010, filed Nov. 24, 2009, and entitled "SYSTEMS, DEVICES, AND METHODS UTILIZING

STRETCHABLE ELECTRONICS TO MEASURE TIRE OR ROAD SURFACE CONDITIONS."

Kim, D. H. et al. (2010). Dissolvable films of silk fibroin for ultrathin conformal bio-integrated electronics. *Nature Materials*, 9, 511-517.

Omenetto, F. G. and D. L. Kaplan. (2008). A new route for silk. *Nature Photonics*, 2, 641-643.

Omenetto, F. G., Kaplan, D. L. (2010). New opportunities for an ancient material. *Science*, 329, 528-531.

Halsed, W. S. (1913). Ligature and suture material. *Journal of the American Medical Association*, 60, 1119-1126.

Masuhiro, T., Yoko, G., Masaobu, N., et al. (1994). Structural changes of silk fibroin membranes induced by immersion in methanol aqueous solutions. *Journal of Polymer Science*, 5, 961-968.

Lawrence, B. D., Cronin-Golomb, M., Georgakoudi, I., et al. (2008). Bioactive silk protein biomaterial systems for optical devices. *Biomacromolecules*, 9, 1214-1220.

Demura, M., Asakura, T. (1989). Immobilization of glucose oxidase with *Bombyx mori* silk fibroin by only stretching treatment and its application to glucose sensor. *Biotechnology and Bioengineering*, 33, 598-603.

Wang, X., Zhang, X., Castellot, J. et al. (2008). Controlled release from multilayer silk biomaterial coatings to modulate vascular cell responses. *Biomaterials*, 29, 894-903.

U.S. patent application Ser. No. 12/723,475 entitled "SYSTEMS, METHODS, AND DEVICES FOR SENSING AND TREATMENT HAVING STRETCHABLE INTEGRATED CIRCUITRY," filed Mar. 12, 2010.

U.S. patent application Ser. No. 12/686,076 entitled "Methods and Applications of Non-Planar Imaging Arrays," filed Jan. 12, 2010.

U.S. patent application Ser. No. 12/636,071 entitled "Systems, Methods, and Devices Using Stretchable or Flexible Electronics for Medical Applications," filed Dec. 11, 2009.

U.S. Patent Application publication no 2012-0065937-A1, published Mar. 15, 2012, and entitled "METHODS AND APPARATUS FOR MEASURING TECHNICAL PARAMETERS OF EQUIPMENT, TOOLS AND COMPONENTS VIA CONFORMAL ELECTRONICS."

U.S. patent application Ser. No. 12/616,922 entitled "Extremely Stretchable Electronics," filed Nov. 12, 2009.

U.S. patent application Ser. No. 12/575,008 entitled "Catheter Balloon Having Stretchable Integrated Circuitry and Sensor Array," filed on Oct. 7, 2009.

U.S. patent application Ser. No. 13/336,518 entitled "Systems, Methods, and Devices Having Stretchable Integrated Circuitry for Sensing and Delivering Therapy," filed Dec. 23, 2011.

It should be appreciated that all combinations of the foregoing concepts and additional concepts described in greater detail below (provided such concepts are not mutually inconsistent) are contemplated as being part of the inventive subject matter disclosed herein. It also should be appreciated that terminology explicitly employed herein that also may appear in any disclosure incorporated by reference should be accorded a meaning most consistent with the particular concepts disclosed herein.

BRIEF DESCRIPTION OF THE DRAWINGS

The skilled artisan will understand that the figures, described herein, are for illustration purposes only, and that the drawings are not intended to limit the scope of the disclosed teachings in any way. In some instances, various aspects or features may be shown exaggerated or enlarged to facilitate an understanding of the inventive concepts disclosed herein (the drawings are not necessarily to scale, emphasis instead being placed upon illustrating the principles of the teachings). In the drawings, like reference characters generally refer to like features, functionally similar and/or structurally similar elements throughout the various figures.

FIGS. 10A-10C show cross-sectional layering structure of various components of an example device, according to the principles described herein.

FIGS. 19A-19D shows examples of catheter devices.

DETAILED DESCRIPTION

Figure 1B:
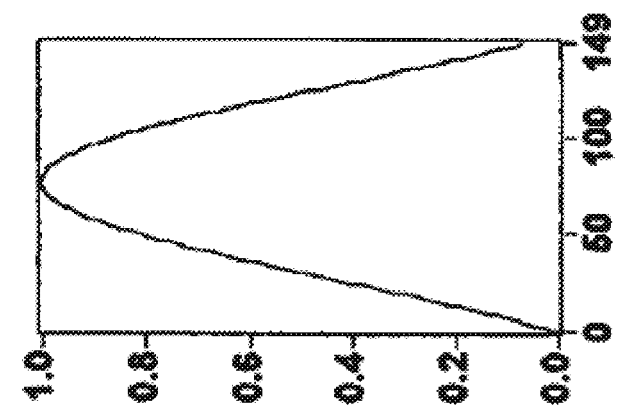
FIGS. 1A-1C show example voltage waveforms for stimulating nerves, according to the principles described herein.

Following below are more detailed descriptions of various concepts related to, and embodiments of, an apparatus and systems for embedding thinned chips in a flexible polymer. It should be appreciated that various concepts introduced above and described in greater detail below may be implemented in any of numerous ways, as the disclosed concepts are not limited to any particular manner of implementation. Examples of specific implementations and applications are provided primarily for illustrative purposes.

As used herein, the term "includes" means includes but is not limited to, the term "including" means including but not limited to. The term "based on" means based at least in part on. As used herein, the term "disposed on" or "disposed above" is defined to encompass "at least partially embedded in."

With respect to substrates or other surfaces described herein in connection with various examples of the principles herein, any references to "top" surface and "bottom" surface are used primarily to indicate relative position, alignment and/or orientation of various elements/components with respect to the substrate and each other, and these terms do not necessarily indicate any particular frame of reference (e.g., a gravitational frame of reference). Thus, reference to a "bottom" of a substrate or a layer does not necessarily require that the indicated surface or layer be facing a ground surface. Similarly, terms such as "over," "under," "above," "beneath" and the like do not necessarily indicate any particular frame of reference, such as a gravitational frame of reference, but rather are used primarily to indicate relative position, alignment and/or orientation of various elements/components with respect to the substrate (or other surface) and each other. The terms "disposed on" "disposed in" and "disposed over" encompass the meaning of "embedded in," including "partially embedded in." In addition, reference to feature A being "disposed on," "disposed between," or "disposed over" feature B encompasses examples where feature A is in contact with feature B, as well as examples where other layers and/or other components are positioned between feature A and feature B.

Renal denervation therapy can be used to disrupt the renal nerve through ablation, including through applying energy in the form of RF energy, heating, or cryo (extreme cold) to the nerves. This can be done by inserting a tube or catheter into the groin and guiding the device into the renal artery. The renal denervation procedure ordinarily is not configured to provide measurement of the efficacy of the process.

Other non-limiting examples of ablation energy that can be applied using a catheter with flow sensing: according to the principles described herein include radiofrequency (RF), ultrasound energy, cryoablation, drug-based ablation, alcohol injection, microwave energy ablation, and light-based ablation (laser energy).

While the description of the assessment is described relative to a procedure on a renal artery, the assessment of the efficacy of a procedure can be performed in other systems. For example, an assessment described herein for determining the efficacy of a procedure using flow measurements can be applied to procedures being performed in other tissue lumen, such as pulmonary veins, coronary arteries, peripheral blood vessels, cardiac lumen, and any other lumen in which flow can be assessed.

An increase in blood flow in the renal artery can be used as an indicator of the degree of efficacy of a renal sympathetic denervation (RSDN) procedure. For example, an indication of an increase in the rate of blood flow can be considered an indicator that a RSDN procedure is effective in achieving the desired degree and/or amount of denervation in the tissue being targeted. Such an indication of the degree of efficacy can be extrapolated to signal an endpoint to the procedure if the flow-rate of blood is approaching the desired level. As another example, an indication of little or no change in the rate of blood flow can be considered an indicator that a RSDN procedure is ineffective or marginally effective in achieving the desired degree and/or amount of denervation in the tissue being targeted. Such an indication of the degree of efficacy can be extrapolated used in a determination of an expected number of additional procedures to be performed to achieve the desired outcome, or potential changes that could be made to make the RSDN procedure more effective.

According to the principles described herein, example devices and methods are described for determining the efficacy of a renal denervation procedure is disclosed that relates to monitoring changes in blood flow rates before and after the procedure.

This disclosure relates to flow measurement systems that can be implemented to determine the efficacy of interventional procedures such as renal denervation. According to an example and method described herein, a change in flow rate of blood through the tissue lumen can be used to provide an indication of the effectiveness of a procedure performed on the renal artery. The procedure can be any procedure to disrupt the renal nerve, e.g., through ablation, including through applying energy in the form of RF energy, heating, or cryo (extreme cold) to the nerves. An example application of a flow measurement system, apparatus and method described herein is to provide an indication to a physician that the clinical procedure is successful.

According to the principles described herein, example devices and methods are described for use in establishing a clinical endpoint in a procedure in a renal artery. In an example system and method, a measure of blood flow in a renal artery prior to the procedure and/or subsequent to the procedure can be used to provide an indication of an efficacy of a procedure. In another example, blood flow measurements during a pre-procedure cycle and/or during a post-procedure cycle can be used to establish a clinical endpoint for the procedure being performed to disrupt the renal nerve, e.g., through ablation, including through applying energy in the form of RF energy, heating, or cryo (extreme cold) to the nerves.

Sympathetic nerve activity controls blood pressure and flow by virtue of vasoconstriction. Delivery of electrical stimulation to renal sympathetic nerves can, in turn, be used to stimulate the renal nerves and cause a modulation in renal blood flow. According to the principles described herein, example devices and methods are described for measuring changes in local blood flow and/or pressure during a procedure, such as but not limited to a RSDN procedure.

At present, most forms of high-performance electronics and electrodes are rigid, bulky and have cylindrical cuff-like formats that are inherently low density and incompatible with the soft, complex topologies of arteries. In various example implementations, novel multifunctional catheter devices are described that include novel microfabrication technology to build arrays of soft and flexible nanomembrane flow sensing and electrode elements that can be used to provide feedback about renal blood flow, while concurrently delivering pacing energy and ablation energy. In various examples described herein, novel design strategies and fabrication techniques are described that use inorganic semiconductor processes to achieve high performance flexible flow sensor and electrode arrays on catheter devices, such as but not limited to, spiral shaped and balloon catheters that concurrently measure flow and apply RF energy and pacing energy inside a renal artery.

Figure 1A:
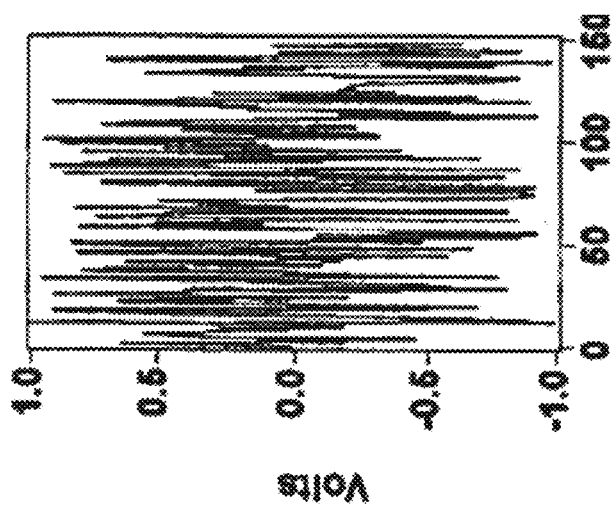
Figure 2:
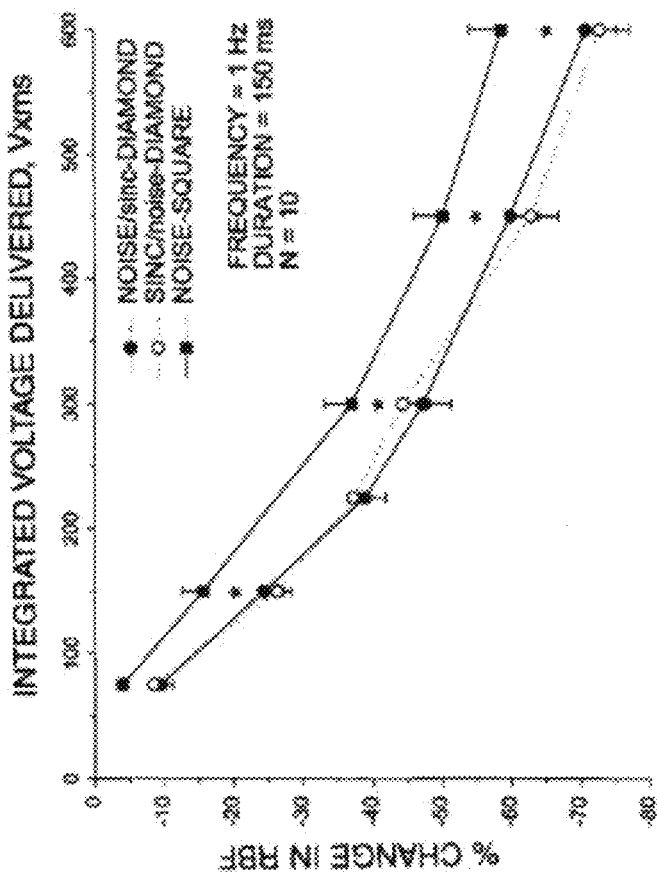
FIG. 2 shows a plot of percent changes of renal blood flow as a function of integrated voltage being delivered during pacing, according to the principles described herein.
Figure 1C:
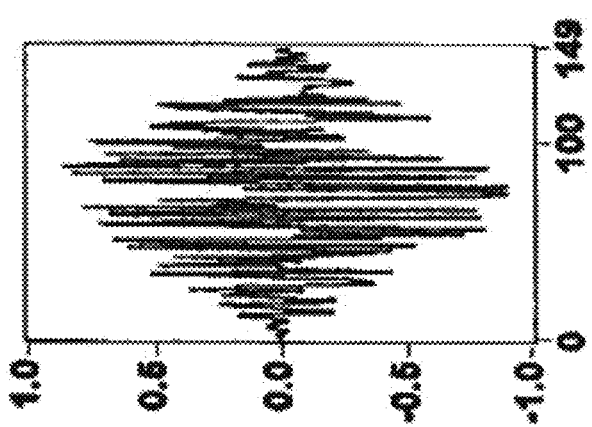

An example catheter device according to the principles described herein can include at least one pacing electrode. In a pacing procedure, a potential is applied to a portion of tissue proximate to a nerve to stimulate blood flow. FIGS. 1A-1C show example voltage waveforms that can be used to stimulate the nerves. FIG. 2 shows a plot of percent changes of renal blood flow as a function of integrated voltage being delivered during pacing. FIGS. 1A-1C and FIG. 2 demonstrate that blood flow can be changed in the renal artery due to programmed nerve stimulation (during pacing). In an example, such pacing can be performed during a procedure performed according to the principles described herein. For example, at least one pacing electrode can be disposed on an example catheter device described herein to provide an electrical stimulation to tissue, e.g., in a region of a nerve source, prior to, during, and/or following a procedure. That procedure can be any procedure that disrupts the renal nerve through ablation, including through applying energy in the form of RF energy, heating, or cryo (extreme cold) to the nerves.

Example devices and methods are described that combine, on a single catheter device, components to perform a procedure on a tissue and components to perform sensing of the flow rate of blood, according to the principles described herein. Example devices and methods are also described that combine on a single catheter device, components to perform nerve stimulation (such as using pacing electrodes) and components to perform sensing of the flow rate of blood, according to the principles described herein. In an example, an indication of\the flow rate of blood based on measurements using the catheter device can be used to establish a clinical endpoint during a procedure, including a RSDN procedure.

Figure 3B:
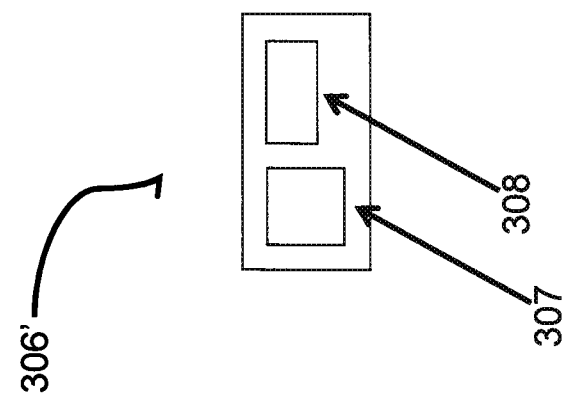
FIG. 3B shows an example flow sensor. according to the principles described herein.
Figure 3A:
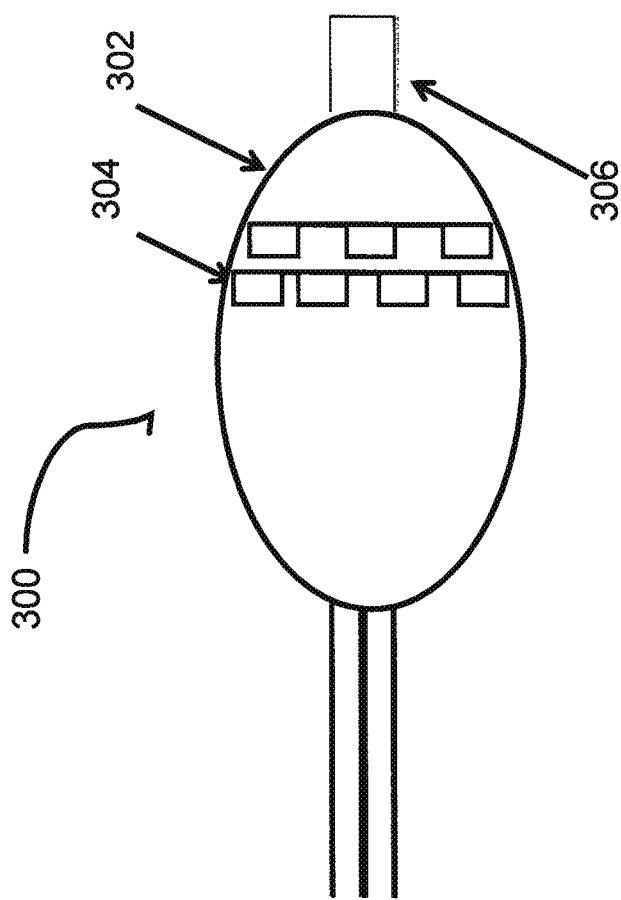
FIG. 3A shows an example device that can be used to perform a procedure, according to the principles described herein.

FIG. 3A shows an example device 300 that can be used to perform a procedure according to the principles described herein. The example device 300 includes an inflatable and/or expandable body 302, a flow sensor 304 disposed on a portion of the inflatable and/or expandable body 302, and an electronic circuit 306 disposed on the inflatable and/or expandable body 302. The electronic circuit 306 includes a number of components that accommodate expanding of the inflatable and/or expandable body 302. In FIG. 3A, the flow sensor 304 is illustrated as being disposed on a distal portion of the inflatable body. In another example, the flow sensor can be disposed on or proximate to a proximal portion of the inflatable and/or expandable body.

In an example implementation, the flow sensor can be a formed as illustrated in FIG. 3B. FIG. 3B shows an example flow sensor 306' that includes a heating element 307 disposed proximate to a temperature sensor 308. In various examples, the heating element 307 can be separated from the temperature sensor 308 by about 1 mm, about 2 mm, about 3 mm, about 5 mm, about 8 mm, about 10 mm, about 12 mm, about 18 mm, about 24 mm, about 30 mm or more.

Temperature sensor 308 can be a thermocouple, a resistance temperature detector (RTD) temperature sensor, a junction potential temperature sensor (including sensors that use a voltage measure across a junction as an indicator of temperature), a thermistor, an integrated-circuit temperature sensor (including a LM35-series temperature sensor), or a semiconductor temperature sensor. Example flow sensor 306' can provide a measure of the flow rate of blood in a tissue lumen based on temperature measurements of the temperature sensor. In operation, the heating element is used to maintain the temperature sensor at a specified temperature measurement value. Any fluid flowing past the heating element and temperature sensor can cause some change or fluctuation in the temperature measurement of the temperature sensor. The heating element is configured such that it tried to maintain the temperature sensor at the stable specified temperature reading. A change in the fluid flow rate that causes some fluctuation in the reading of the temperature sensor causes the heating element to increase of decrease its heat output to bring the temperature sensor to its specified reading. A faster flow rate of the fluid (e.g., the blood) in the region of the flow sensor can cause the heating element to increase its heat output. A slower flow rate of the fluid (e.g., the blood) in the region of the flow sensor can cause the heating element to decrease its heat output. As a result, a change in the operating point of the heating element can be used to provide an indication of the flow rate of the fluid measurement of the temperature sensor can be used to provide an indication of the flow rate of fluid proximate to the inflatable and/or expandable body 302.

The example flow sensors according to the principles described herein can include a temperature sensor proximate to a thermal 'radiation' source. According to any of the example systems, methods and apparatus described herein, non-limiting examples of heating elements that can provide the thermal radiation include any form of heater that can be coupled with a catheter, including a resistive heater or a thermoelectric heater.

In any example device according to the principles described herein, the temperature sensor can include at least one of a resistance temperature detector (RTD) temperature sensor, a thermocouple, a junction potential temperature sensor (including sensors that use a voltage measure across a junction as an indicator of temperature), a thermistor, an integrated-circuit temperature sensor (including a LM35-series temperature sensor), and a semiconductor temperature sensor. In various examples, a sensor of known impedance is used. Other non-limiting examples of sensors that can be used according to any of the systems and methods described herein include vapor deposited gold resistors and ceramic thermistors. In another example, other materials such as foils can be used.

In an example, a calibration standard can be developed for the flow sensor 306', to correlate the operating point of the heating element to a flow rate. For example, training samples can be used to convert a flow measurement, each training sample being a fluid caused to flow at a specific flow rate. For a given amount and/or rate of change of operating point of the heating element by the heating element, the operating point of the flow sensor is obtained for each training sample. The flow rate of each training sample is known (given that it is pre-set for the training samples). The amount and/or rate of heating supplied by the heating element is also known. The calibration standard can be developed to correlate the known heating supplied to the known flow rate to obtain calibration data. The example calibration standard can be used to convert a flow sensor measurement to a flow rate for a fluid having similar properties as the fluid used in the training standard.

In an example implementation, the examples device of FIGS. 3A and 3B can further include a flow sensor that is disposed on a portion of a catheter that is coupled to the proximal portion of the inflatable and/or expandable body.

In an example, the electronic circuit 306 can include a number of electrodes disposed on the inflatable and/or expandable body 302. The electrodes can be used to perform a procedure according to the principles described herein. For example, at least one of the electrodes can be a radiofrequency (RF) electrode that delivers RF energy to a portion of the tissue surface that is proximate to the RF electrode. According to the principles described herein, the delivered RF energy is used to modify the tissue, including to disrupt a renal nerve.

In another example, the device 300 can include components to perform a procedure using other modalities. For example, the device 300 can include components to disrupt the renal nerve, e.g., through ablation, including through applying energy in the form of RF energy, heating, or cryo (extreme cold) to the nerves.

In another example, the electronic circuit 306 of device 300 can include at least one pacing electrode. The pacing electrode can be implemented to deliver an electrical stimulation to a portion of a tissue (such as but not limited to a renal artery) proximate to the pacing electrode. As described above, the pacing electrode can be used to stimulate nerve at different stages of a procedure. For example, the electrical stimulation from the pacing electrode(s) can be applied to the portion of the tissue to stimulate nerves prior to delivery of an energy to disrupt the nerves, such as but not limited to through ablation, including through applying energy in the form of RF energy, heating, or cryo (extreme cold) to the nerves. In another example, the electrical stimulation from the pacing electrode(s) can be applied to the portion of the tissue to stimulate nerves subsequent to delivery of an energy to disrupt the nerves, such as but not limited to through ablation, including through applying energy in the form of RF energy, heating, or cryo (extreme cold) to the nerves.

In another example, the electronic circuit 306 can also include temperature sensors, each temperature being disposed proximate to an electrode of the electronic circuit 306.

In another example, the device 300 can include one or more other components disposed on the inflatable and/or expandable body such as, but not limited to, a pacing electrode, a light-emitting device, a contact sensor, an image detector, a pressure sensor, a biological activity sensors, a temperature sensor, or any combination thereof.

Figures 4A, 4B:
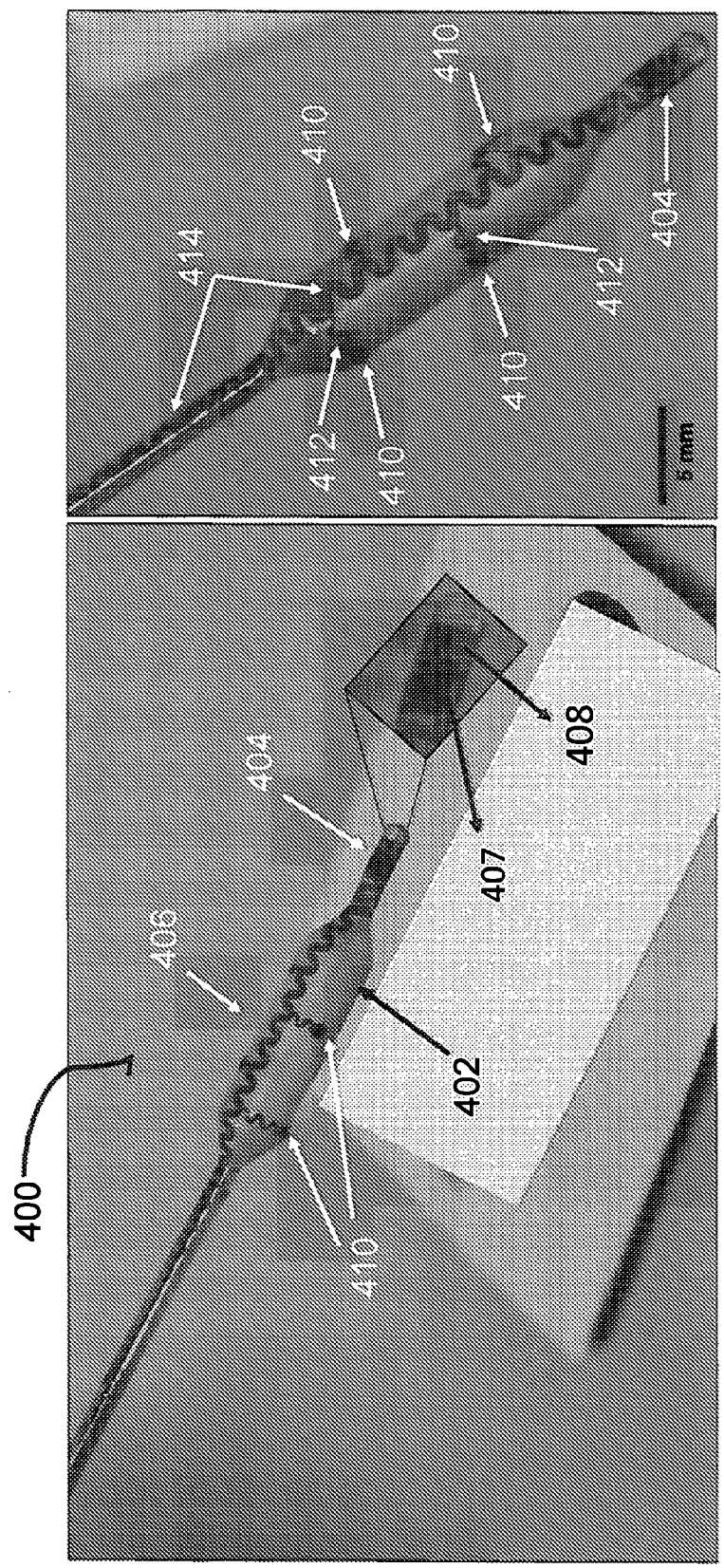
FIGS. 4A and 4B show example implementation of an example device, according to the principles described herein.

FIGS. 4A and 4B show a non-limiting example implementation of an example device example device 400. The example device 400 includes an inflatable and/or expandable body 402, a flow sensor 404 disposed on a portion of the inflatable and/or expandable body 402, and an electronic circuit 406 disposed on the inflatable and/or expandable body 402. The electronic circuit 406 includes a number of components that accommodate expanding of the inflatable and/or expandable body 402. As shown in FIGS. 4A and 4B, the flow sensor 404 can be being disposed on a distal portion of the inflatable and/or expandable body 402. As a non-limiting example, a portion of the distal region of the expandable and/or inflatable structure can be extended to form a protrusion. The flow sensor 404 can be mounted on the protrusion. In another example, the flow sensor 404 can be disposed on or proximate to a proximal portion of the inflatable and/or expandable body.

In an example implementation, the flow sensor 404 can be a formed as including a heating element 407 disposed proximate to a temperature sensor 408. In various examples, the heating element 407 can be separated from the temperature sensor 408 by about 1 mm or about 2 mm. As a non-limiting example, the heating element 407 can be a temperature-controlled heating element. As a non-limiting example, the temperature sensor 408 can be a thermistor.

In the non-limiting example of FIGS. 4A and 4B, the electronic circuit can include a number of electrodes 410 disposed on the inflatable and/or expandable body 402. The electrodes can be used to perform a procedure according to the principles described herein. For example, at least one of the electrodes 410 can be a radiofrequency (RF) electrode that delivers RF energy to a portion of the tissue surface that is proximate to the RF electrode. According to the principles described herein, the delivered RF energy is used to modify the tissue, including to disrupt a renal nerve.

As shown in the non-limiting example of FIGS. 4A and 4B, the electronic circuit 406 of the example device 400 can include stretchable interconnects 412 disposed on the surface of the inflatable and/or expandable body 402. As shown in FIG. 4B, the stretchable interconnects can be used to electrically couple at least one of the plurality of electrodes 410 to an external circuit.

As shown in the non-limiting example of FIGS. 4A and 4B, the electronic circuit 406 of the example device 400 can also include a main bus 414. As shown in FIG. 4B, the stretchable interconnects 412 electrically couple the electrodes 410 to the man bus 414. As also shown in FIG. 4B, the main bus 414 can extend beyond the inflatable and/or expandable body 402 to facilitate electrical coupling of the electrodes 410 to an external circuit.

In another example, the at least one of the electrodes 410 of electronic circuit 406 of device 400 can be a pacing electrode. The pacing electrode can be implemented to deliver an electrical stimulation to a portion of a tissue (such as but not limited to a renal artery) proximate to the pacing electrode. As described above, the pacing electrode can be used to stimulate nerve at different stages of a procedure. For example, the electrical stimulation from the pacing electrode(s) can be applied to the portion of the tissue to stimulate nerves prior to delivery of an energy to disrupt the nerves, such as but not limited to through ablation, including through applying energy in the form of RF energy, heating, or cryo (extreme cold) to the nerves. In another example, the electrical stimulation from the pacing electrode(s) can be applied to the portion of the tissue to stimulate nerves subsequent to delivery of an energy to disrupt the nerves, such as but not limited to through ablation, including through applying energy in the form of RF energy, heating, or cryo (extreme cold) to the nerves.

In another example, the device 400 can include components to perform a procedure using other modalities. For example, the device 400 can include components to disrupt the renal nerve, e.g., through ablation, including through applying energy in the form of RF energy, heating, or cryo (extreme cold) to the nerves.

In another example, the device 400 can include one or more other components disposed on the inflatable and/or expandable body such as, but not limited to, a pacing electrode, a light-emitting device, a contact sensor, an image detector, a pressure sensor, a biological activity sensors, a temperature sensor, or any combination thereof.

In another example, the device 400 can also include temperature sensors, each temperature being disposed proximate to an electrode 410 of the electronic circuit 406.

Figure 5:
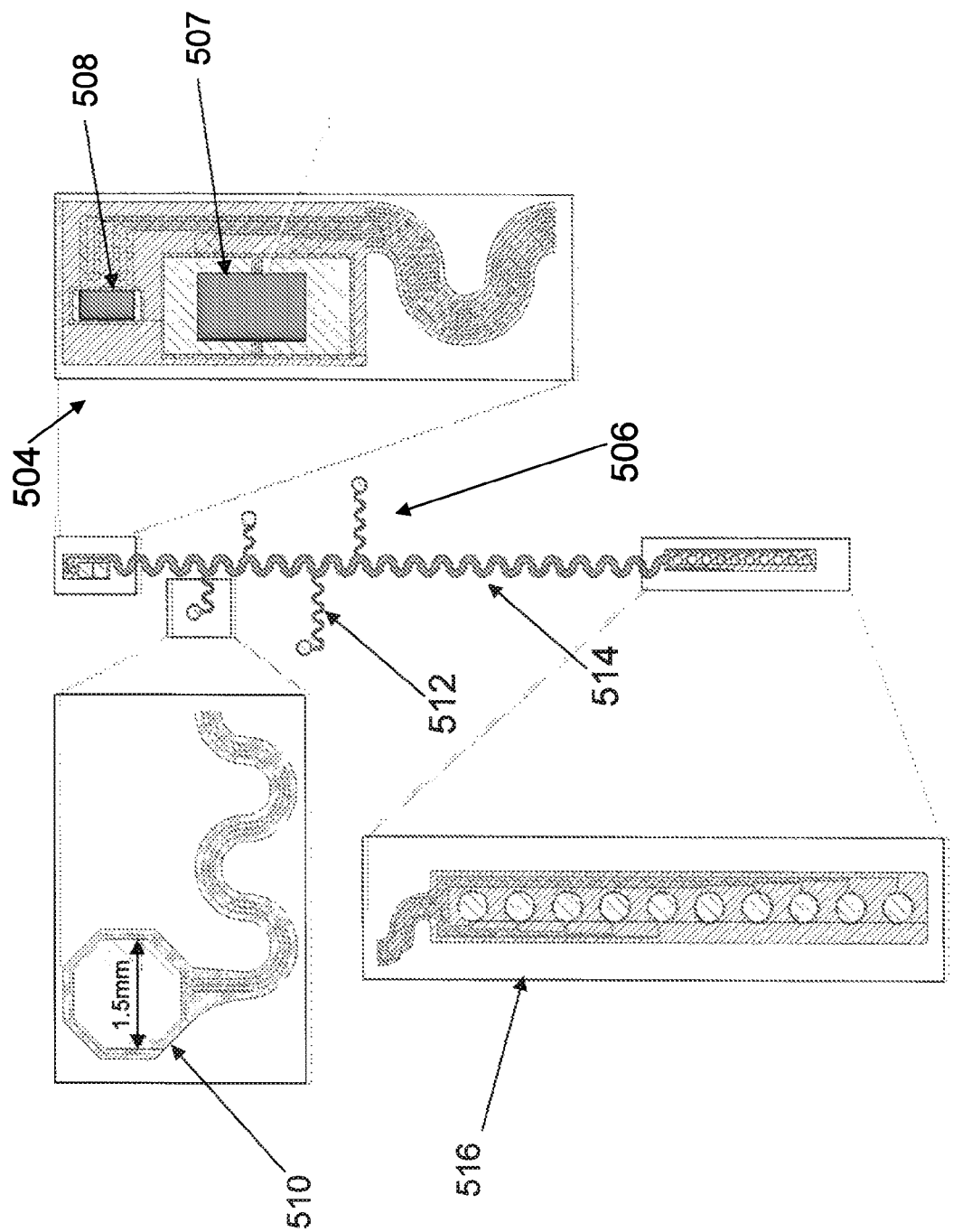
FIG. 5 shows an example implementation of an electronic circuit and flow sensor, according to the principles described herein.

FIG. 5 shows a non-limiting example implementation of an electronic circuit 506 and flow sensor 504 that can be disposed on a catheter and extend to a shaft of an example device according to the principles described herein. The electronic circuit 506 includes a number of electrodes 510. In various examples, the electrodes 510 can be conformable electrodes that conform to the surface of the inflatable and/or expandable body. As shown in FIG. 5, the flow sensor 404 includes a heating element 507 disposed proximate to a temperature sensor 808. As a non-limiting example, the heating element 507 can be a temperature-controlled heating element. As a non-limiting example, the temperature sensor 508 can be a thermistor.

In the non-limiting example of FIG. 5, at least one of the electrodes 510 can be a radiofrequency (RF) electrode that delivers RF energy to a portion of the tissue surface that is proximate to the RF electrode. According to the principles described herein, the delivered RF energy is used to modify the tissue, including to disrupt a renal nerve. At least one of the electrodes 510 can be a pacing electrode that delivers an electrical stimulation to a nerve, as described herein.

As shown in the non-limiting example of FIG. 5, the electronic circuit 506 includes stretchable interconnects 512 disposed on the surface of the inflatable and/or expandable body. The stretchable interconnects 512 can be used to electrically couple at least one of the plurality of electrodes 510 to an external circuit.

As also shown in the non-limiting example of FIG. 5, the electronic circuit 506 also includes a main bus 514. As shown in FIG. 5, the stretchable interconnects 512 electrically couple the electrodes 510 to the man bus 514. As also shown in FIG. 5, the main bus 514 include connection pads 516 that facilitate electrical coupling of the electrodes 510 to an external circuit.

Figure 6A:
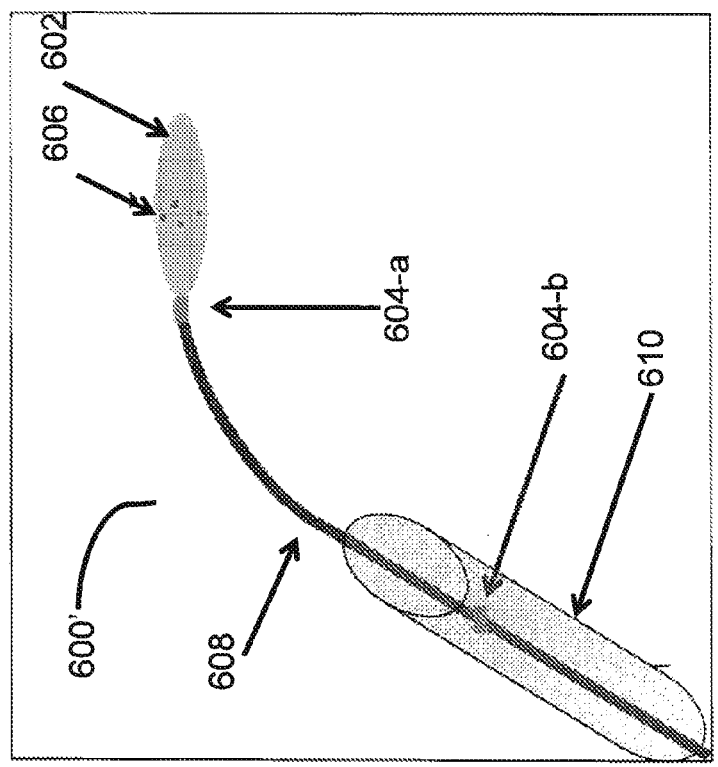
FIG. 6A shows another example device, according to the principles described herein.

FIG. 6A shows another example device 600 that can be used to perform a procedure according to the principles described herein. The example device 600 includes an inflatable and/or expandable body 602, a pair of flow sensors 604-$a$ and 604-$b$, and an electronic circuit 606 disposed on the inflatable and/or expandable body 602. The device 600 is coupled to a distal portion of a shaft 608. The electronic circuit 606 includes a number of components that accommodate expanding of the inflatable and/or expandable body 602. In FIG. 6A, one of the flow sensor 604-$a$ is shown to be disposed on a proximal portion of the inflatable body. The other flow sensor (reference flow sensor 604-$b$) is shown to be disposed on a portion of shaft 608 at some distance away from the inflatable and/or expandable body 602. In the example implementation of FIG. 6A, the flow rate can be measured based on comparison of the measurement of the pair of flow sensors 606-$a$ and 606-$b$. For example, the flow rate can be measured based on comparison of voltage measurements of the pair of flow sensors 606-$a$ and 606-$b$.

Figure 6B:
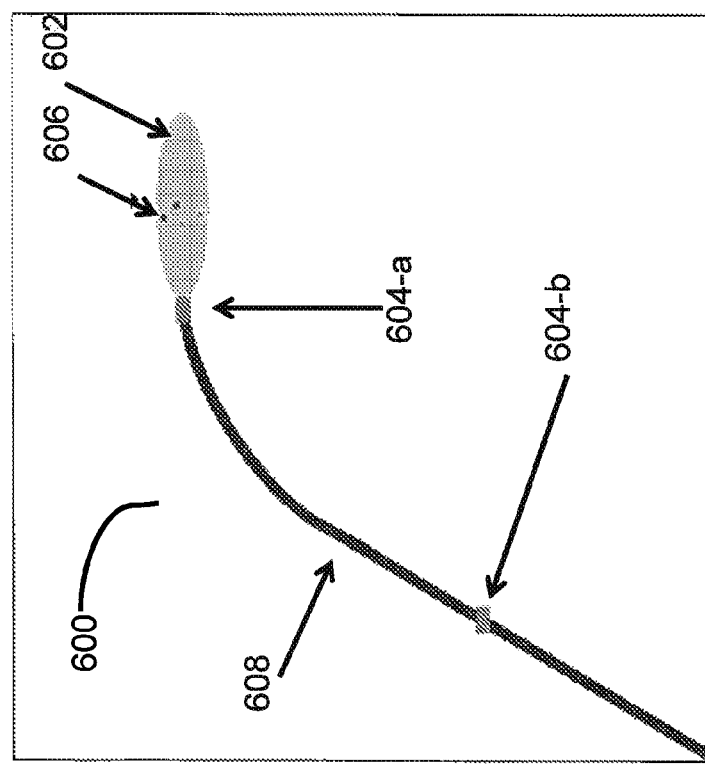
FIG. 6B shows another example device, according to the principles described herein.

FIG. 6B shows another example device 600' that can be used to perform a procedure according to the principles described herein. Example device 600' includes an inflatable and/or expandable body 602, a pair of flow sensors 604-$a$ and 604-$b$, an electronic circuit 606 disposed on the inflatable and/or expandable body 602, and a shaft 608, the same components as example device 600, and they are not repeated. Example device 600' also includes a shaft 610 that can be disposed over reference electrode 604-$b$ during a procedure or a flow measurement. The example device 610 also can be retracted to such an extent that reference flow sensor 604-$b$ is exposed.

In the various examples described herein, the reference sensor can be positioned on the shaft at a location that can be covered by a sheath. FIG. 6B shows a non-limiting example of a catheter device that includes a sheath member that can be positioned to cover at least a portion of the reference sensor. In an example implementation, this distance can be determined as greater than or equal to about 10 cm away from the proximal end of the balloon. In another example implementation, this distance can be determined as less than about 10 cm away from the proximal end of the balloon. For example, the reference flow sensor 604-$b$ can be positioned at a distance away on the shaft of the catheter that is at least about 5 cm, at least about 8 cm, at least about 10 cm, at least about 13 cm, at least about 15 cm or more. In an example implementation, a sheath can be included and used to guide, introduce and steer the catheter. The sheath can be a member that surrounds at least a portion of the circumference of the shaft of the catheter and/or can be co-axial with the shaft of the catheter. During a procedure, the reference sensor can be maintained under the sheath. The sheath can be configured to provide a stable known environment and provide a chamber that can include blood in the absence of flow. In this example, blood enters the sheath but flow can be halted by the presence of a stopcock or flow switch. The blood can be maintained at body temperature but does not flow, thereby providing a useful comparison in proximity of the reference sensors. The measurement performed using the reference sensor in this environment of blood that is not flowing can serve as a reference for comparison to the renal artery sensor.

The internal shaft near the reference sensor can include surface features in the form of bumps or tracks that provide channels for the blood. The blood forms an insulating layer on the reference sensor, allowing a reference quiescent blood temperature to be measured. The surface features can be designed and configured to allow blood to circulate as freely and prevent the shaft from making contact with the sheath in that area. For example, the shaft may include one or more spacers (also referred to as protuberances) to maintain the shaft spaced apart from a portion of the surface of the sheath. The spacing apart of the shaft from the sheath helps to maintain a static layer of blood static between the sheath and the shaft.

Figures 7A, 7B:
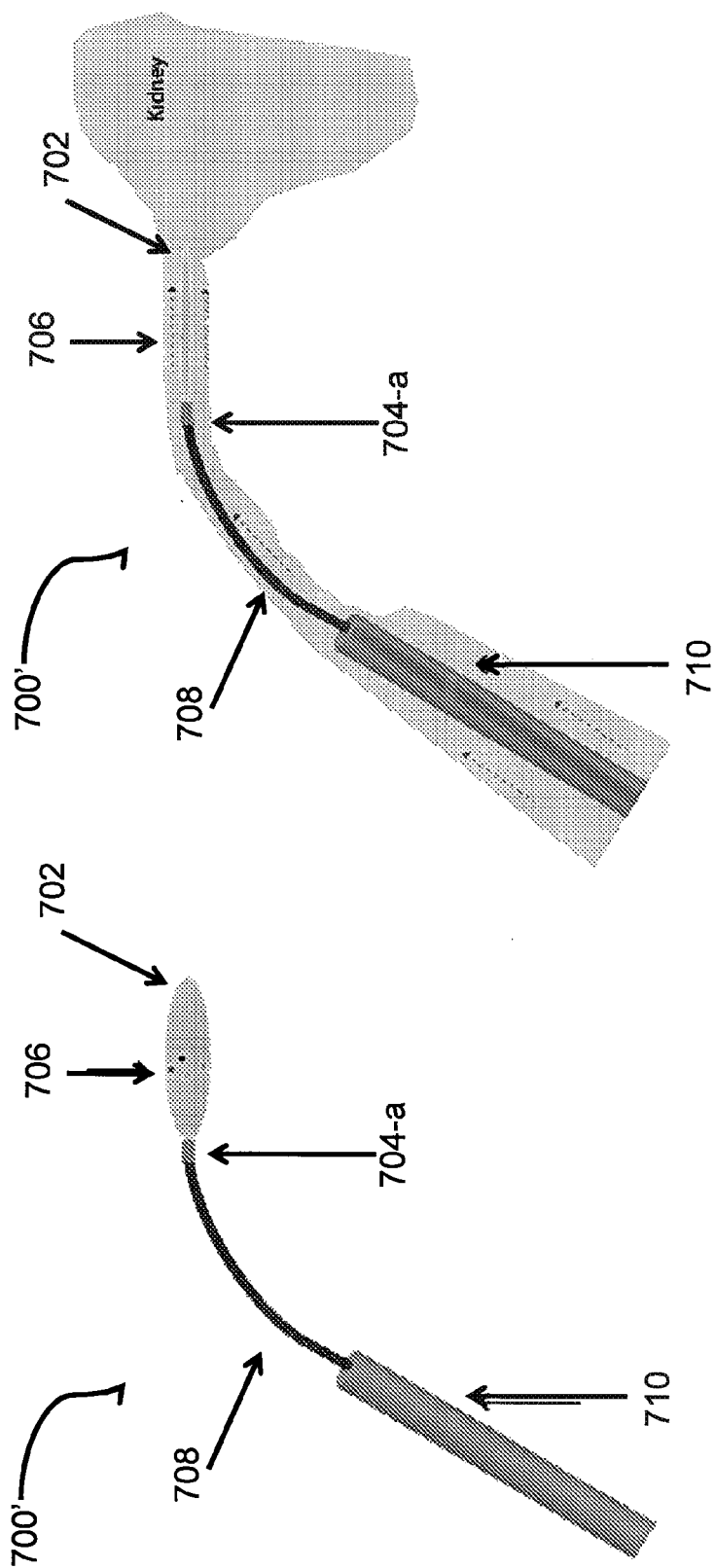
FIGS. 7A and 7B illustrate an operation of the flow sensors of FIGS. 6A-6B, according to the principles described herein.

FIGS. 7A and 7B illustrate an operation of the flow sensors of FIGS. 6A-6B. FIG. 7A shows an example device 700 that includes an inflatable and/or expandable body 702, a pair of flow sensors 704-$a$ and 704-$b$, an electronic circuit 706 disposed on the inflatable and/or expandable body 702, a shaft 708 and a sheath 710. Flow sensor 704-$b$ is coupled to the shaft and covered by the sheath 710. In the example of FIG. 7B, blood flows in the aorta and renal artery, yet blood remains static in the sheath due to a stopcock or flow switch. This allows a differential measurement of flow in the renal artery versus static flow in the sheath. It also allows for better use of dynamic range since the measurement is limited between the two sensors. As also shown in FIG. 7B, the inflatable or expandable structure can be deflated or retracted at the time of flow sensor measurement.

In an example implementation, the method in connection with FIGS. 7A and 7B can be used to resolve small changes in temperature in the body. An example system, apparatus and method according to the principles described herein can be used to measure the signal of interest in connection with a procedure and reject information that does not relate to the signal of interest, thereby increasing resolution and reducing the requirements for expensive signal processing.

An example system, apparatus and method according to the principles described herein can be used to measure differential flow, such as described in connection with FIGS.

7A and 7B. In an example implementation, two (or more) sensors are used to measure flow via a change in flow sensor operating point. As shown in FIGS. 7A and 7B, at least one reference sensor can be placed on the shaft of a catheter used to perform a measurement described herein. The non-limiting example catheter can include one or more renal artery flow sensors and/or one or more other sensors, including one or more ablation components and/or one or more pacing electrodes. The reference sensor can be disposed about the inflatable or expandable member of the catheter, such as but not limited to a balloon, an expandable mesh, or a deployable netting. The reference sensor can be disposed at a sufficient separation distance away from the proximal end of the balloon so that the reference sensor is covered by the sheath of the catheter when it is proximate to the tissue of the body. One or more renal artery sensors can be positioned at or near the proximal end of the balloon. Each measurement taken can be compared or displayed in reference to a measurement of the reference sensor.

Figure 8:
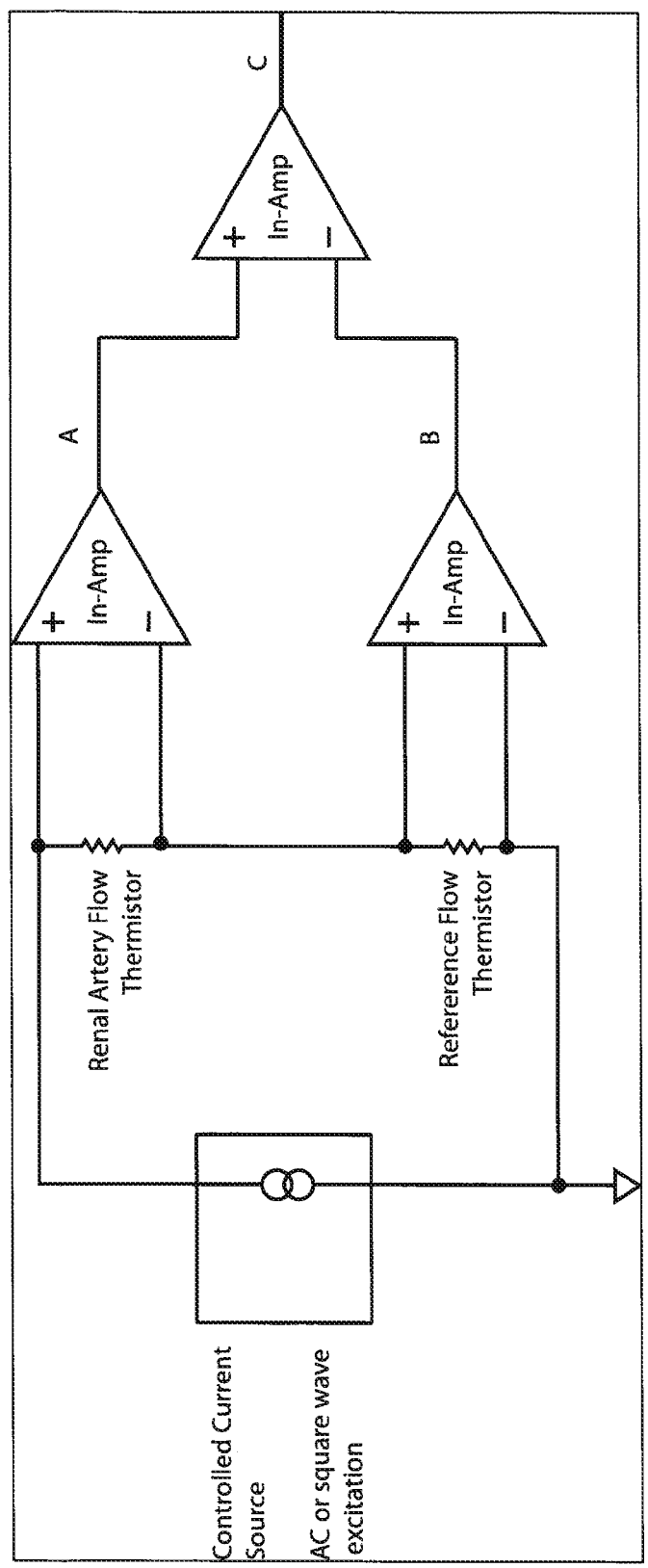
FIG. 8 shows an example simplified schematic of a differential pre-amplifier, according to the principles described herein.

Systems, methods and apparatus are described herein that can be used to increase the dynamic range of measurements by focusing on the signal of interest. In an example implementation, each flow sensor, including any reference sensor, can be excited using the same controlled current source. In an example implementation, each sensor can be measured using an instrumentation amplifier. FIG. 8 shows a non-limiting example simplified schematic of a differential pre-amplifier that can be used to measure differences in voltages. The example differential pre-amplifier circuitry can be implemented to compare measurements of flow sensors according to the principles of FIGS. 3A-7B. In this non-limiting example, the flow sensors can include thermistors. In other examples, the flow sensors can include at least one of a resistance temperature detector (RTD) temperature sensor, a thermocouple, a junction potential temperature sensor (including sensors that use a voltage measure across a junction as an indicator of temperature), an integrated-circuit temperature sensor (including a LM35-series temperature sensor), and a semiconductor temperature sensor. In various examples, a sensor of known impedance is used. Other non-limiting examples of sensors that can be used according to any of the systems and methods described herein include vapor deposited gold resistors and ceramic thermistors. In another example, other materials such as foils can be used.

In the example of FIG. 8, the difference in the voltage can be measured between the flow sensors (such as but not limited to the thermistor) that are driven by an excitation current. Signal C is the difference between the signal from the flow sensor proximate to the inflatable and/or expandable body (renal flow sensor measurement-signal A) and the signal from the reference flow sensor (reference flow sensor measurement-signal B).

The instrumentation amplifiers can be used to reject common-mode signals, thereby providing a higher fidelity signal. In a non-limiting example, an apparatus or system described herein can include thermistors that are well matched (used as the flow sensors in this example). The absolute values of the thermistor measurements can be used. A benefit of measuring a reference thermistor and renal artery thermistor can be improvement of the dynamic range by measuring the difference of the values between the sensors as compared to using the absolute values. Limiting the measurements between the reference and the renal artery sensor can facilitate improvement of the dynamic range of the measurements.

An example implementation to perform a measurement is described. In an example, the flow sensors are of known impedances, and application of an excitation current using the flow sensors creates a voltage that is measured using instrumentation amplifiers. The amplifiers are used to measure a voltage correlating to a flow rate. Changes in blood flow can result in a change in operating set point in at least one of the flow sensors. By comparing the value of voltage measured using the reference sensor to the value of voltage measured using a flow sensor disposed proximate to the expandable and/or inflatable body, the flow rate can be quantified. Through this comparison, the instrument voltage in the absence of flow also can be removed. In an example, the value of voltage measured using the reference sensor is subtracted from the renal artery sensor voltage to provide an indication of the instrument voltage in the absence of flow. In an example where a reference flow sensor is surrounded by a sheath, blood in the sheath is physically static. That is, it is not flowing and remains at body temperature. Blood in the renal artery is also at body temperature but flows at some rate (desired to be measured).

The differential voltage comparison can be computed based on the flow sensor measurement data as follows:

Differential Measurement $(C)$=Renal Artery Sensor Voltage $(A)$–Reference Sensor Voltage$(B)$ It also can be expressed as: $C=A-B$ Effectively, in an example implementation, the equation can be expressed as:

Differential Measurement=(Voltage$_{BodyTemp}$+Voltage$_{RenalFlow}$)−(Voltage$_{BodyTemp}$+0)

where $V_{SheathFlow}=0$.
Differential Measurement=Voltage$_{RenalFlow}$
A gain can be added at any of the instrumentation amplifiers to increase the amplitude of the signal.

In an example implementation, one or more flow sensors can be calibrated. An offset value between the flow sensors disposed proximate to the inflatable and/or expandable body and the reference flow sensor(s) can be eliminated by placing the catheter in a known temperature and flow rate, and measuring the difference between the two sets of sensors. The measurement can be performed and/or the offset value can be derived at the time of manufacture of the catheter and/or time of assembly of the flow sensors with the inflatable and/or expandable body of the catheter. The offset value can be stored and/or indicated as a written value, or a barcode or other form of identification (ID). In an example, an integrated circuit or memory device or other means can be used to provide this value and ID to a console that is in communication with the catheter (including with the flow sensors disposed on or proximate to the inflatable and/or expandable body). This offset value can be programmed into the catheter. When the catheter is coupled with the console, the console can use the offset value to compensate for an offset in the measurements when calculating flow.

Detecting a change in reading of a thermistor, such as in an example of the implementation described in connection with FIGS. 6A-7B and 8, can provide an indication of the rate of fluid flow. Detecting flow rate change in the renal artery can require high-resolution measurement.

Figure 9:
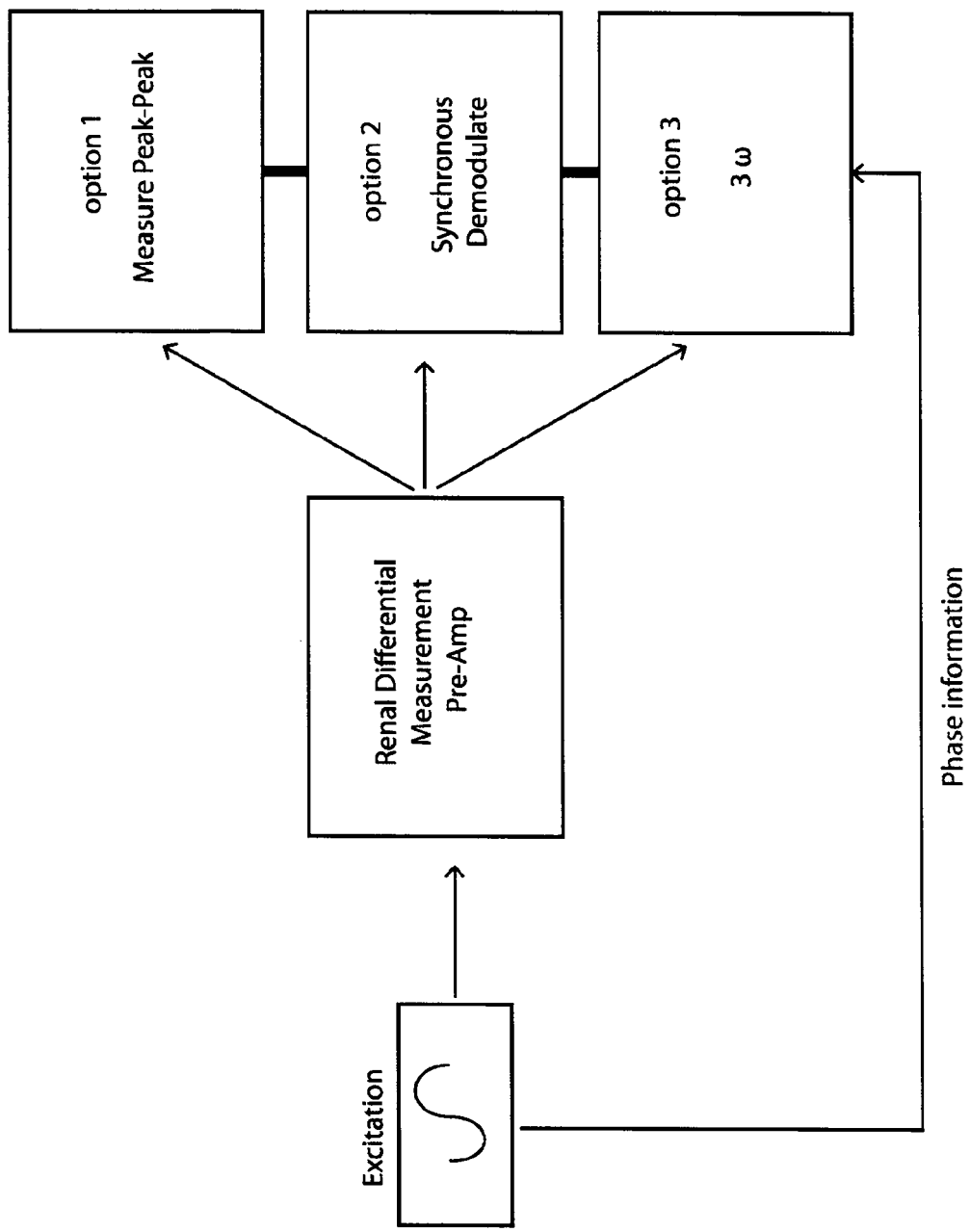
FIG. 9 shows an example operation of a 3-$\omega$ acquisition system, according to the principles described herein.

For example, the differential measurement described in connection with FIGS. 6A-7B and 8 can be used in conjunction with other methods, such as peak-to-peak measurements, synchronous-demodulation (lock-in), and three omega (3ω) methods. In different example implementations, the differential measurement can be used to measure peakto-peak output, or it can be input into a lock-in amplifier or 3ω acquisition system as shown in FIG. 9. The 3ω method can be implemented using a micro-fabricated metal pattern acting as a resistive heater. An alternating current (AC) voltage signal energizes the resistive element at a frequency ω. The periodic heating generates oscillations in the electrical resistance of the metal line at a frequency of 2ω. In turn, this leads to a third harmonic (3ω) in the voltage signal. The third harmonic is used according to an example implementation to determine the magnitude of the temperature oscillations. The temperature oscillations can be used to provide an indication of the flow rate of a fluid. For example, the frequency dependence of these temperature oscillations can be used to derive the thermal properties of the specimen (e.g., the fluid). The data indicative of the thermal properties of the specimen can be used to derive data indicative of the flow rate of the fluid.

In any of the examples described herein, the flow sensor (including the 3-omega sensor) can be disposed on the example device such that the flow sensor is disposed within a mid-point of a tissue lumen when the example device is disposed within the lumen. The mid-point of the lumen in tissue (including the renal artery lumen) can be the location of maximum flow velocity). The central positioning of the flow sensor can facilitate more accurate measured of fluid flow rate by sampling the area of maximum flow.

In an example, any system or device according to the principles described herein may be entirely or at least partially encapsulated by an encapsulating material, such as a polymer material (including any of the polymer materials described herein). An encapsulating material can be any material that can be used to laminate, planarize, or encase at least one component of a system or device described herein, including any electronic or other type of component. For example, a method of fabricating any system or device according to the principles described herein can further include encapsulating the system or device. In an example, an encapsulating material can be disposed over, or otherwise applied to, an device that includes an inflatable and/or expandable body and the electronic circuit or a plurality of electrodes. In an example, a polyurethane can be used as the encapsulating material. In another example, the encapsulating material can be the same material as the material for the inflatable and/or expandable body. Encapsulating any portion of the systems or device described herein can be useful to enhance the mechanical stability and robustness of the system or device, or to maintain electronic performance of the electronic components of the system or device against a stress or strain applied to the system or device during use.

In any of the example devices according to the principles described herein, the encapsulating material can be formed from any material having elastic properties. For example, the encapsulating can be formed from a polymer or polymeric material. Non-limiting examples of applicable polymers or polymeric materials include, but are not limited to, a polyimide, a polyethylene terephthalate (PET), a silicone, or a polyurethane. Other non-limiting examples of applicable polymers or polymeric materials include plastics, elastomers, thermoplastic elastomers, elastoplastics, thermostats, thermoplastics, acrylates, acetal polymers, biodegradable polymers, cellulosic polymers, fluoropolymers, nylons, polyacrylonitrile polymers, polyamide-imide polymers, polyarylates, polybenzimidazole, polybutylene, polycarbonate, polyesters, polyetherimide, polyethylene, polyethylene copolymers and modified polyethylenes, polyketones, poly(methyl methacrylate, polymethylpentene, polyphenylene oxides and polyphenylene sulfides, polyphthalamide, polypropylene, polyurethanes, styrenic resins, sulphone based resins, vinyl-based resins, or any combinations of these materials. In an example, a polymer or polymeric material herein can be a DYMAX® polymer (Dymax Corporation, Torrington, Conn.). or other UV curable polymer, or a silicone such as but not limited to ECOFLEX® (BASF, Florham Park, N.J.).

For applications in biomedical devices, the encapsulant should be biocompatible. The stretchable interconnects can be embedded in a polyimide that also acts as a mechanical reinforcement.

In an example, any of the systems or device according to the principles herein can be disposed on the inflatable and/or expandable body such that a functional layer of the system or device lies at a neutral mechanical plane (NMP) or neutral mechanical surface (NMS) of the system or device. The NMP or NMS lies at the position through the thickness of the device layers for the system or device where any applied strains are minimized or substantially zero. In an example, the functional layer of a system or device according to the principles described herein includes the plurality of sensing elements, the coupling bus, and/or the stretchable electronic system that includes the flexible annular interconnect and the plurality of electrodes.

The location of the NMP or NMS can be changed relative to the layer structure of the system or device through introduction of materials that aid in strain isolation in various layers of the system or device. In various examples, polymer materials described herein can be introduced to serve as strain isolation materials. For example, the encapsulating material described hereinabove can be used to position the NMP or NMS, e.g., by varying the encapsulating material type and/or layer thickness. For example, the thickness of encapsulating material disposed over the functional layers described herein may be modified (i.e., decreased or increased) to depress the functional layer relative to the overall system or device thickness, which can vary the position of the NMP or NMS relative to the functional layer. In another example, the type of encapsulating, including any differences in the elastic (Young's) modulus of the encapsulating material.

In another example, at least a partial intermediate layer of a material capable of providing strain isolation can be disposed between the functional layer and the inflatable and/or expandable body to position the NMP or NMS relative to the functional layer. In an example, the intermediate layer can be formed from any of the polymer materials described herein, aerogel materials or any other material with applicable elastic mechanical properties.

Based on the principles described herein, the NMP or NMS can be positioned proximate to, coincident with or adjacent to a layer of the system or device that includes the strain-sensitive component, such as but not limited to the functional layer. The layer can be considered "strain-sensitive" if it is prone to fractures or its performance can be otherwise impaired in response to a level of applied strain. In an example where the NMP or NMS is proximate to a strain-sensitive component rather than coincident with it, the position of the NMP or NMS may still provide a mechanical benefit to the strain-sensitive component, such as substantially lowering the strain that would otherwise be exerted on the strain-sensitive component in the absence of strain isolation layers. In various examples, the NMS or NMP layer is considered proximate to the strain-sensitive component that provides at least 10%, 20%, 50% or 75% reduction in strain in the strain-sensitive component for a given applied strain, e.g., where the inflatable body is inflated.

In various examples, the encapsulating material and/or the intermediate layer material may be disposed at positions coincident with the strain-sensitive component, including in the functional layer. For example, portions of the encapsulating material and/or the intermediate layer material may be interspersed with the strain-sensitive component, including at positions within the functional layer.

In any of the example devices according to the principles described herein, portions of the stretchable interconnects, the electrodes and portions of the main bus can be formed from a conductive material. In any of the examples described herein, the conductive material can be but is not limited to a metal, a metal alloy, a conductive polymer, or other conductive material. In an example, the metal or metal alloy of the coating may include but is not limited to aluminum, stainless steel, or a transition metal (including copper, silver, gold, platinum, zinc, nickel, titanium, chromium, or palladium, or any combination thereof) and any applicable metal alloy, including alloys with carbon. In other non-limiting example, suitable conductive materials may include a semiconductor-based conductive material, including a silicon-based conductive material, indium tin oxide or other transparent conductive oxide, or Group III-IV conductor (including GaAs). The semiconductor-based conductive material can be doped.

In any of the example structures described herein, the stretchable interconnects can have a thickness of about 0.1 μm, about 0.3 μm, about 0.5 μm, about 0.8 μm, about 1 μm, about 1.5 μm, about 2 μm or greater. The buffer structure and/or flexible base can have a thickness of about 5 μm, about 7.5 μm, about 9 μm, about 12 μm or greater. In any example herein, the encapsulant can have a thickness of about 100 μm, about 125 μm, about 150 μm, about 175 μm, about 200 μm, about 225 μm, about 250 μm, about 300 μm or greater.

FIGS. 10A and 10B show cross-sectional layering structure of various components of the example devices described herein, which can be microfabricated. FIG. 10A shows the layering structure of an electrode, which includes a polymer layer 1002, a layer of conductive material 1004, and an annular structure of a polymer 1006 about a perimeter of the electrode. FIG. 10B shows the layering structure of a stretchable interconnect, which includes a polymer layer 1002, a layer of conductive material 1004, and a layer of a polymer 1006. FIG. 10C shows the layering structure of a flow sensor disposed on the inflatable and/or expandable body, which includes a polymer layer 1002, a layer of conductive material 1004, a layer of a polymer 1006, a flow sensor 1008, and an encapsulating layer 1010. In an example, the components can be fabricated on a carrier substrate, released from the carrier substrate, and disposed on the inflatable and/or expandable body.

A non-limiting example fabrication process for the example device of FIGS. 10A and 10B is as follows. The electrode can be fabricated using a microfabrication and transfer printing process to be between about 1 micron and about 5 microns thick. The sensors can be 3-omega sensors (described below) and the surface mount components (including the flow sensors) can be fabricated using use pure gold or Cu—Au—Ni fabrication techniques. The fabricated electronic structure are integrated on the surface of an inflatable and/or expandable body (such as but not limited to a balloon of a catheter). In the example device structures of FIGS. 10A and 10B, the polyimide can be about 25 microns in thickness. A polyurethane, formed of a resin and a solvent, can be used as an encapsulant to planarize the array of electrodes and other components on the surface of the inflatable and/or expandable body. The encapsulant helps to provide durability during sheath insertion of the example device into a tissue lumen.

In an example, the micro-fabricated flow sensors, electrode arrays (including ablation RF electrodes), electronics and other components of the example device are ultrathin, and have mechanical properties substantially similar or matched with the mechanical properties of the inflatable or expandable surface.

Systems and methods are described for performing a procedure on a tissue, including a renal artery, using any example device described herein. The example method includes disposing an example device in proximity to the tissue, applying the treatment to be applied to the tissue, and recording the flow measurement of the flow sensor as described herein to provide an indication of the flow rate of a fluid in proximity to the example device.

In an example, the treatment can include applying an ablation or applying energy in the form of RF energy, heating, or cryo (extreme cold) to the tissue. In an example, the treatment is performed to disrupt nerves in proximity to the tissue.

In an example, the method can be performed with an example device that includes a flow sensor element configured as a heating element in proximity to a temperature sensor. In this example, the operating point of the heating element can be monitored to provide an indication of flow rate. In an example, the recording of the flow measurement of the flow sensor can be performed subsequent to applying the RF energy to the surface of the tissue proximate to the RF electrode. In another example, the recording of the flow measurement of the flow sensor can be performed prior to the applying of the RF energy to the surface of the tissue proximate to the RF electrode.

In an example, the temperature measurement may be performed before and after application of the RF energy, to obtain an indication of the flow rate of the fluid (such a blood) prior to and subsequent to the treatment procedure being performed.

In an example, systems, methods and devices for monitoring an efficacy of, determining a clinical endpoint for, a procedure. According to the principles described herein, the procedure can be any procedure to disrupt the renal nerves, such as but not limited to an ablation, including through applying energy in the form of RF energy, heating, or cryo (extreme cold) to the nerves. The procedure is not performed completed blindly with no feedback on the success of the procedure, with potential risk of damage to tissue. The example systems, methods and devices described herein provide an assessment of a renal denervation procedure based on renal hemodynamics (including based on the measures of fluid flow rate).

In any example described herein, an assessment module is provided according to the systems and methods described herein, where the assessment module includes a processor and a memory storing processor executable instructions. Execution of the processor executable instructions causes the assessment module to perform the activities associated with any method described herein, including using the data indicative of flow rate to provide an indication of the efficacy of a clinical procedure.

In an example, the example method can include using an indication of an increase in the flow rate of the fluid subsequent to the performance of the treatment as an indicator of the efficacy of the treatment procedure to disrupt the nerves (including the efficacy of applying the RF energy to the tissue). For example, a pre-set value of fluid flow rate or clinically desired percentage increase in flow rate can be used as an indicator of the efficacy of the procedure, including being used as an indication of an end-point of performance of the procedure. As a non-limiting example, a baseline flow rate can be measured using the flow sensors described herein prior to performing the procedure to disrupt the nerves. A desired pre-set value of fluid flow rate or clinically desired percentage increase in flow rate can be determined based on the baseline flow rate. For example, the pre-set value of fluid flow rate or clinically desired percentage increase in flow rate can be set as the amount needed to return the flow rate to an average, mean or median range of values for renal blood flow rate. In a feedback assessment, the procedure can be performed, the flow rate subsequently re-measured/re-determined based on flow sensor measurement data according to the principles described herein, and the re-measured flow rate compared to the pre-set value of fluid flow rate or clinically desired percentage increase in flow rate. If the desired pre-set value of fluid flow rate or clinically desired percentage increase in flow rate is not attained, the procedure can be repeated and the flow rate re-measured. If the desired pre-set value of fluid flow rate or clinically desired percentage increase in flow rate is attained, it signals the endpoint, and the procedure can be discontinued. In an example, the example method can include using an indication of little or no increase in the flow rate of the fluid subsequent to the performance of the treatment as an indicator of a lack of the efficacy of the treatment (including the efficacy of applying the RF energy to the tissue), or as an indication that the treatment procedure should be repeated, discontinued or modified. If the desired pre-set value of fluid flow rate or clinically desired percentage increase in flow rate is not attained, the procedure can be modified to achieve the desired outcome. In an example, the feedback of performing the procedure, re-measuring the flow rate and comparing to the pre-set value of fluid flow rate or clinically desired percentage increase in flow rate can be repeated until the endpoint is signaled.

While the assessment is described relative to a procedure on a renal artery, the assessment of the efficacy of a procedure can be performed in other systems. For example, an assessment described herein for determining the efficacy of a procedure using flow measurements can be applied to procedures being performed in other tissue lumen, such as pulmonary veins, coronary arteries, peripheral blood vessels, cardiac lumen, and any other lumen in which flow can be assessed.

In an example, the method can include activating at least one pacing electrode of the example device to deliver an electrical stimulation to a portion of the tissue proximate to the pacing electrode. For example, the method can include delivering the electrical stimulation to the portion of the tissue proximate to the pacing electrode prior to recording a flow measurement (including recording a flow measurement of a flow sensor).

Figure 11:
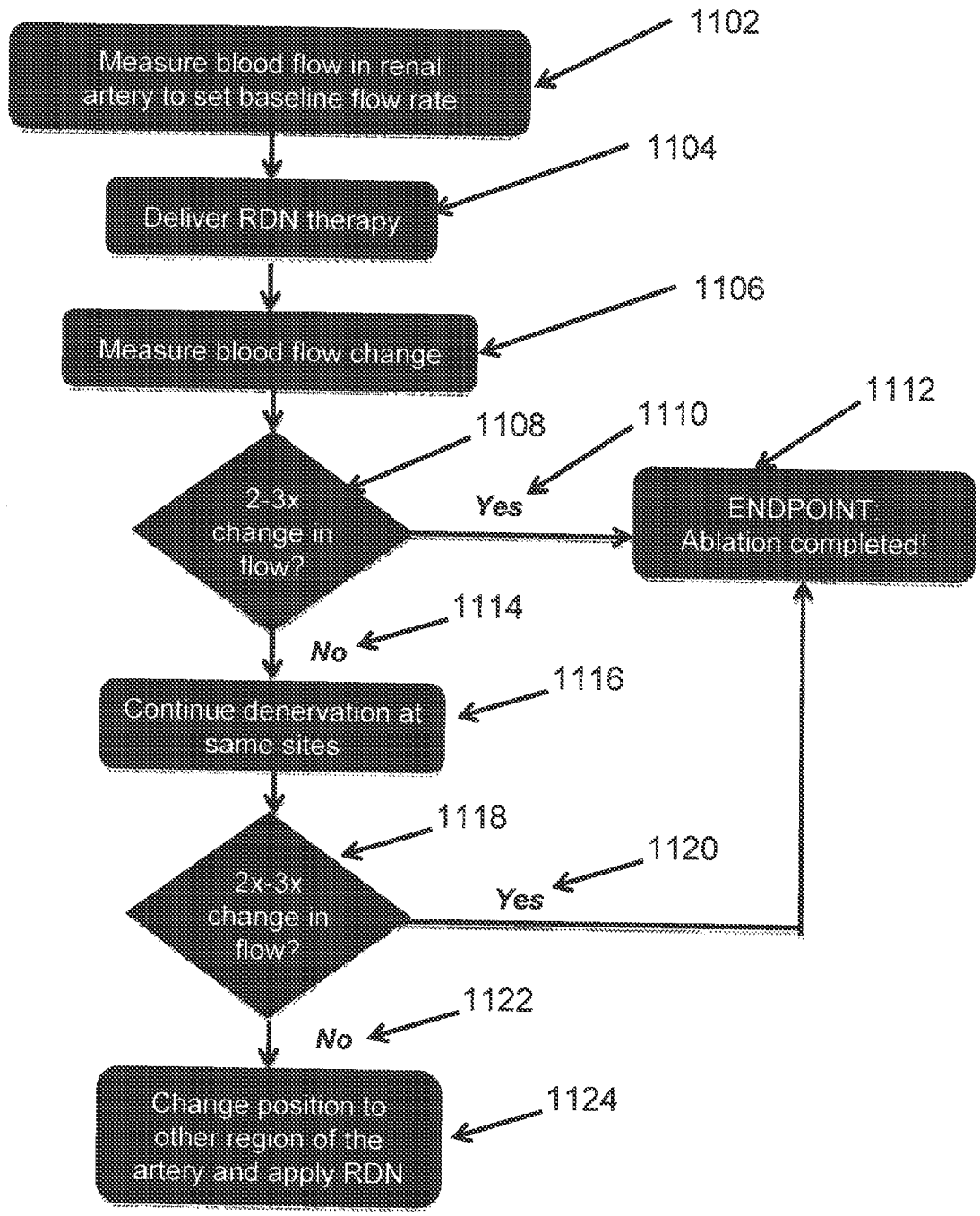
FIG. 11 shows a flowchart of an example method for performing an example assessment, according to the principles described herein.

A non-limiting example process sequence, for performance of a procedure on renal artery tissue using an example device that is configured as a balloon catheter, is as follows:
Perform initial measurement (e.g., obtain a baseline flow)
Inflate catheter balloon to block blood flow
Measure renal flow using any of the example devices or methods described herein
Pace the renal artery (e.g., apply electrical signals to tissue using electrodes of the system)
Deflate catheter balloon
Measure "pre-ablation" flow using any of the example devices or methods described herein
Inflate catheter balloon
Perform ablation of the renal artery (e.g., apply energy to tissue to induce lesions and necrosis, including RF energy, heating, and cryoablation)
Deflate catheter balloon
Measure "post-ablation" flow using any of the example devices or methods described herein A non-limiting example process sequence, for renal denervation on renal artery tissue using an example device that is configured as a balloon catheter, is as follows:
Pace the renal artery (e.g., apply electrical signals to tissue using electrodes of the system)
Measure "pre-ablation" flow rate using any of the example devices or methods described herein
Perform ablation of the renal artery (e.g., apply energy to tissue to induce lesions and necrosis, including RF energy, heating, and cryoablation)
Pace the renal artery (e.g., apply electrical signals to tissue using electrodes of the system)
Measure "post-ablation" flow rate using any of the example devices or methods described herein The flowchart of FIG. 11 shows another non-limiting example method for performing an assessment during performance of a procedure, including an ablation procedure. In this example, a two-fold or three-fold increase in blood flow rate in the renal artery is the pre-set condition used as an indicator of an endpoint of applying the procedure in a feedback assessment. In block 1102, a baseline flow rate is measured. In block 1104, a procedure is performed on the tissue, such as but not limited to, a procedure performed using an example device described herein. In block 1106, the flow rate subsequently re-measured/re-determined based on flow sensor measurement data according to the principles described herein. In block 1108, in a feedback assessment, the re-measured flow rate is compared to the pre-set value of fluid flow rate or clinically desired percentage increase in flow rate. If the desired pre-set value of fluid flow rate or clinically desired percentage increase in flow rate is attained (block 1110), it signals the endpoint (1112), and the procedure can be discontinued. If the desired pre-set value of fluid flow rate or clinically desired percentage increase in flow rate is not attained (block 1114), the procedure can be repeated (block 1116) and the flow rate re-measured and compared to the pre-set value of fluid flow rate or clinically desired percentage increase in flow rate (1118). If the desired pre-set value of fluid flow rate or clinically desired percentage increase in flow rate is attained (block 1120), it signals the endpoint (1112), and the procedure can be discontinued. If the desired pre-set value of fluid flow rate or clinically desired percentage increase in flow rate is not attained (block 1122), the procedure can be modified to achieve the desired outcome. For example, as shown in block 1124, the position of the instrument can be changed to some other region of the tissue and the treatment procedure repeated. In an example, the feedback of performing the procedure, re-measuring the flow rate and comparing to the pre-set value of fluid flow rate or clinically desired percentage increase in flow rate can be repeated until the endpoint is signaled.

In an example, an assessment module is provided according to the systems and methods described herein, where the assessment module includes a processor and a memory storing processor executable instructions. Execution of the processor executable instructions causes the assessment module to perform any of the example methods described herein, including in connection with FIG. 11.

Figure 12:
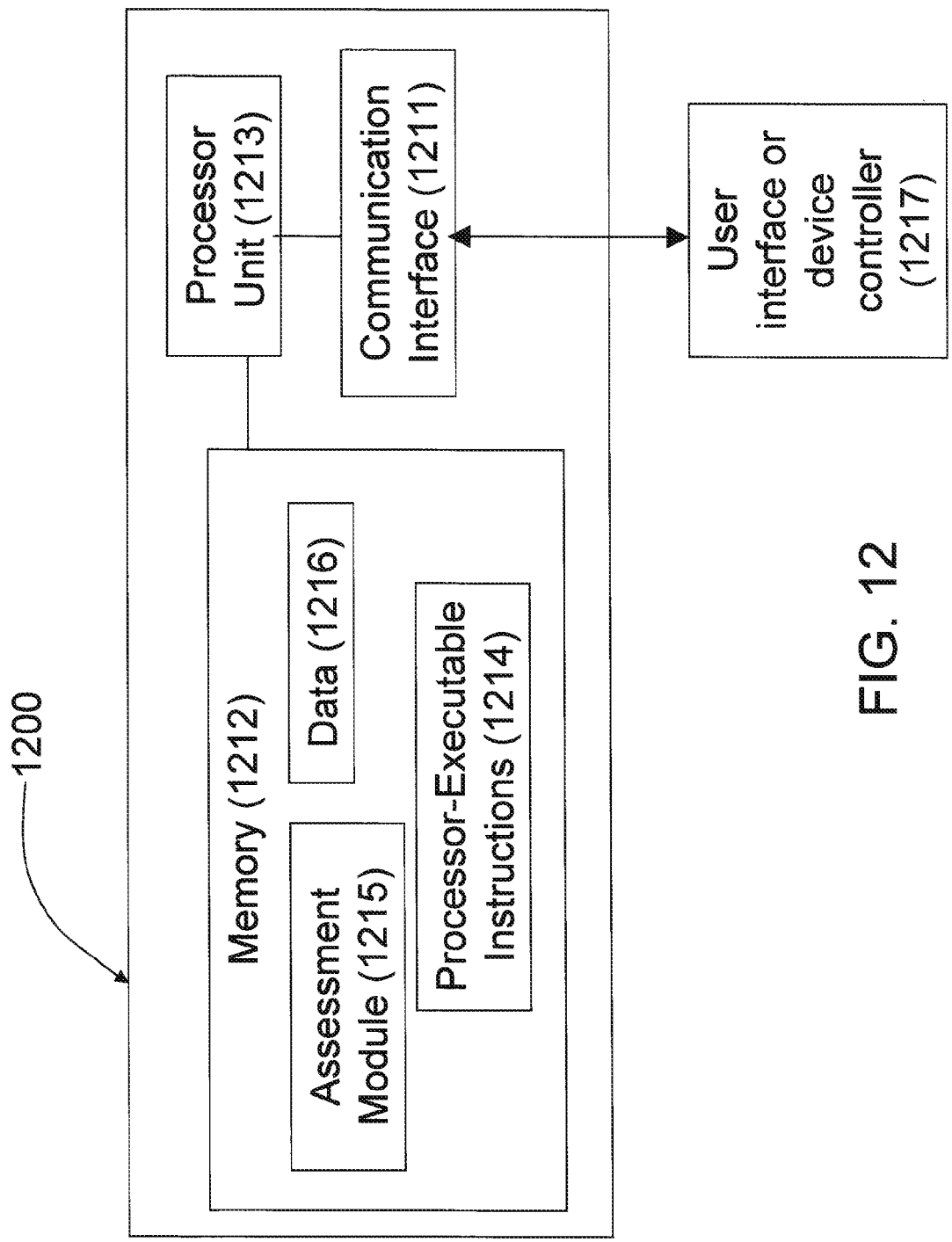
FIG. 12 shows a block diagram of an example system including an assessment module according to the principles described herein.

FIG. 12 shows a block diagram of an example system including an assessment module, according to the systems and methods described herein. A non-limiting example of the system 1200 according to the principles described herein is illustrated in FIG. 12. The system 1200 includes at least one communication interface 1211, at least one memory 1212, and at least one processing unit 1213. The at least one processing unit 1213 is communicatively coupled to the at least one communication interface 1211 and the at least one memory 1212. The at least one memory 1212 is configured to store processor-executable instructions 1214 and an assessment module 1215. As described in greater detail herein, the assessment module 1215 can be applied to determine, based on the flow sensor measurement data 1216, the indication of the flow rate of fluid in the tissue lumen, including to perform a differential comparison of flow sensor measurements or using the measures of flow rate to provide an indication of the efficacy of a procedure being performed on the tissue (such as but not limited to a procedure to disrupt nerves). In a non-limiting example, the at least one processing unit 1213 executes the processor-executable instructions 1214 stored in the memory 1212 at least to provide the feedback described herein during performance of a procedure. The at least one processing unit 1213 also executes processor-executable instructions 1214 to control the memory 1212 to store, or to control the communication interface 1211 to transmit 1217 to, e.g., a user interface or to a controller for any of the example devices described herein, at least one of an indication of the flow rate, an indication of an endpoint for the procedure, an indication of an efficacy of the procedure, and a suggested modification of the procedure.

Figures 13A, 13B:
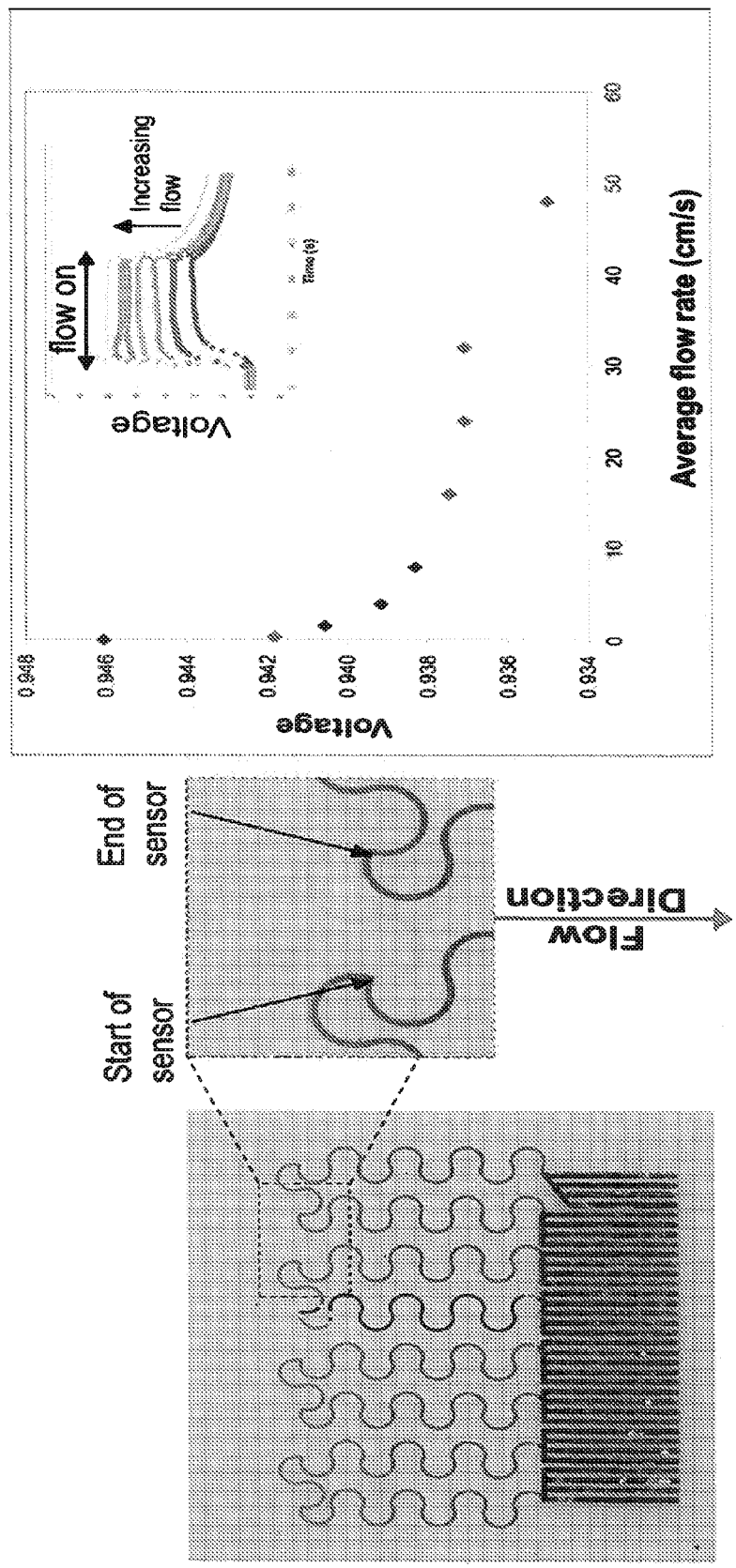
FIG. 13A shows an example flow sensor, according to the principles described herein.
FIG. 13B shows example measurements using an example flow sensor, according to the principles described herein.

In any example implementation according to the principles described herein, readings of 3-omega sensors can be used as the flow sensor on any of the devices described herein to provide an indication of the rate of flow of the fluid. The 3-omega sensors have similar fabrication processing steps as the pacing electrodes or the ablation electrodes. FIG. 13A shows a non-limiting example of a 3-omega sensor. The 3-omega sensors have intricate filamentary patterns, which can survive extreme mechanical bending and twisting and yet maintain performance. The 3-omega sensors measure blood flow by assessing minute changes in local temperature. Example results collected in a perfusion chamber with preset flow rates are shown in FIG. 13B. The 3-omega sensors can be disposed proximate to the inflatable and/or expandable body (including at the distal portion of the catheter). The 3-omega sensor can be disposed on the example device such that the 3-omega sensor is disposed within a mid-point of a tissue lumen (location of maximum flow velocity) and three other locations near the wall of the tissue lumen. Data collected across multiple 3-omega sensors in this configuration can facilitate flow rate measurements at multiple positions inside the tissue lumen. The sensitivity of the 3-omega sensors (such as the example of FIG. 13A) is in the range compatible with blood flow rates that exist in vivo (~5-50 cm/s flow rates).

In any example implementation according to the principles described herein, the flow sensing can be performed using other techniques. For example, an ultrasound measurement can be performed to provide an indication of the rate of flow of fluid pre-renal denervation procedure and/or post-renal denervation procedure to provide the feedback for determining the end-point or a procedure or to determine whether the procedure should be modified. As another example, an optical measurement can be used to provide the indication of the rate of flow of fluid pre-renal denervation procedure and/or post-renal denervation procedure to provide the feedback for determining the end-point or a procedure or to determine whether the procedure should be modified. Other applicable flow sensing technology is a time-of-flight measurement, where the flow behavior of a tracker fluid introduced into the renal artery is measured to used to provide the indication of the rate of flow of fluid pre-renal denervation procedure and/or post-renal denervation procedure.

Fluid flow monitoring before, during and after delivery of nerve pacing and delivery of a treatment according to the principles described herein (including ablation energy) are powerful capability sets, that when offered in a single spiral catheter, can enhance the efficacy of a treatment procedure (including a renal denervation procedure). Variations in blood flow change the local steady-state temperature, which is measured with the 3-omega sensors. Absence of modulation in renal blood flow during pacing can indicate that ablation was successful and enable physicians to determine the end point of the renal denervation procedure.

In an example implementation, flow in a perfusion chamber can be systematically measured that provides programmable fluid volume velocity to test the sensitivity of a measurement system. Fluid flow rates can be systematically characterized at various ambient temperatures, ionic strengths, and viscosities to test how heat flux, electro-osmosis (during electrical stimulation) and fluid boundary layer thickness affect flow. The perfusion chamber can be equipped with electrical sensors that allow concomitant testing of pacing and ablation.

Figure 14:
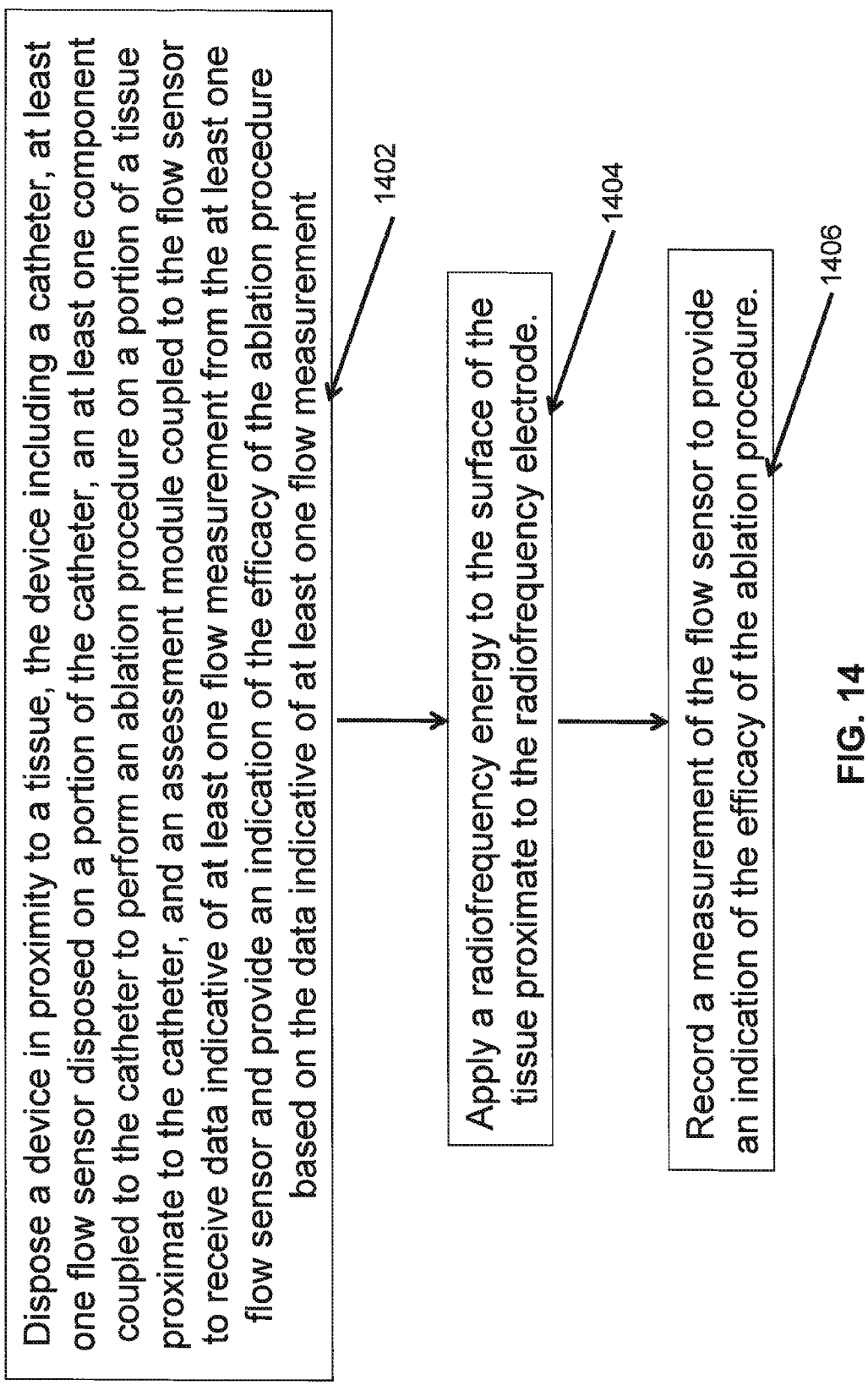
FIG. 14 shows an example method for performing a procedure, according to the principles described herein.

An example method for performing a procedure is described in connection with FIG. 14. The example method includes disposing 1402 an example device according to the principles described herein in proximity to a tissue, the device including a catheter, at least one flow sensor disposed on a portion of the catheter, at least one component coupled to the catheter to perform an ablation procedure on a portion of a tissue proximate to the catheter, and an assessment module coupled to the flow sensor to receive data indicative of at least one flow measurement from the at least one flow sensor and provide an indication of the efficacy of the ablation procedure based on the data indicative of at least one flow measurement. The example method also includes applying 1404 the ablation procedure to the surface of the tissue proximate to the catheter and recording 1406 a measurement of the flow sensor to provide an indication of the efficacy of the ablation procedure.

Figure 15:
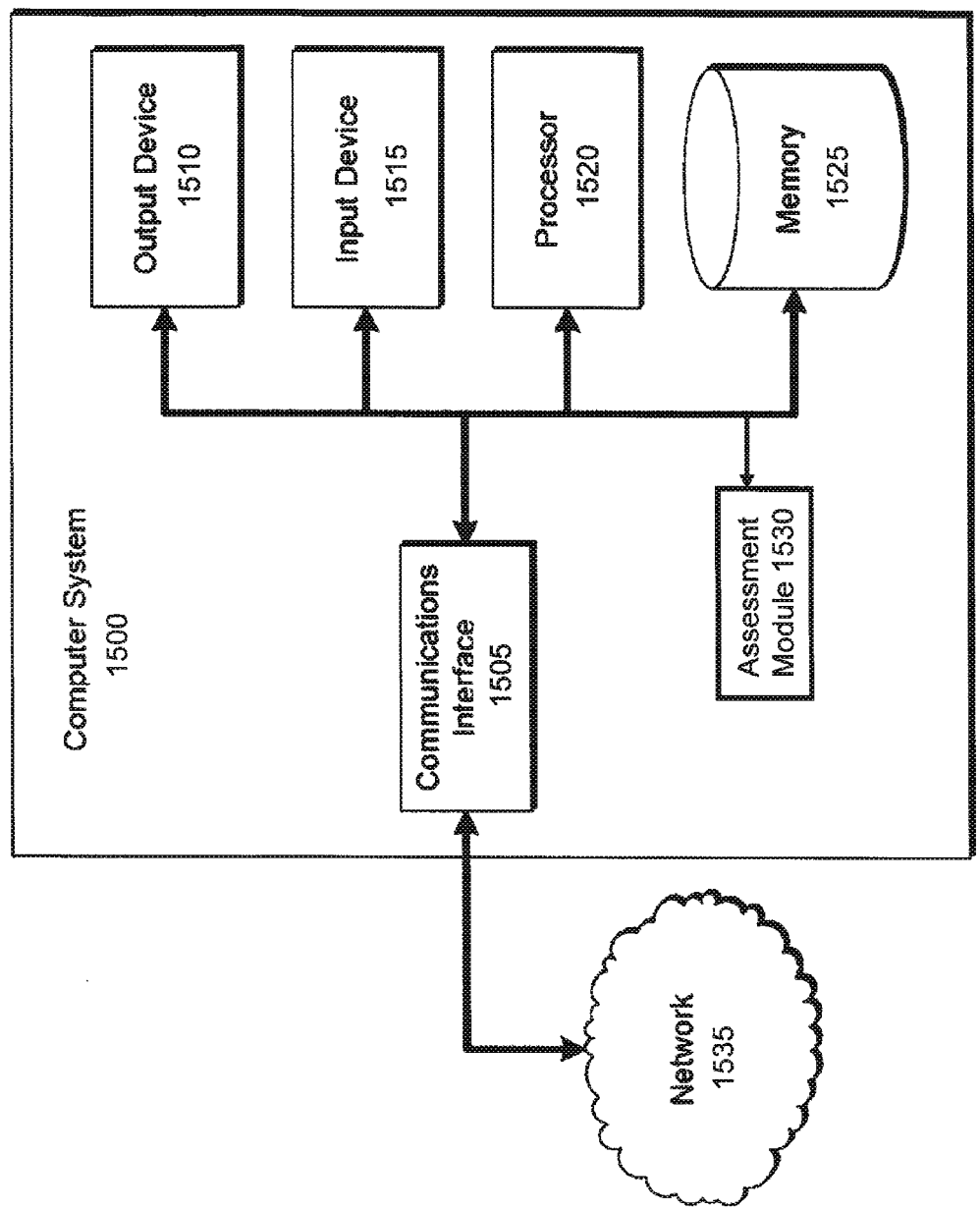
FIG. 15 shows an example architecture of an illustrative computer system, according to the principles described herein

FIG. 15 shows an example architecture of an illustrative computer system 1500 that can be employed to implement any of the systems and methods described herein. The computer system 1500 of FIG. 15 comprises one or more processors 1520 communicatively coupled to memory 1525, one or more communications interfaces 1505, and one or more output devices 1510 (e.g., one or more display units) and one or more input devices 1515.

In the computer system 1500 of FIG. 15, the memory 1525 may comprise any computer-readable storage media, and may store computer instructions such as processor-executable instructions for implementing the various functionalities described herein for respective systems, as well as any data relating thereto, generated thereby, or received via the communications interface(s) or input device(s). The processor(s) 1520 shown in FIG. 15 may be used to execute instructions stored in the memory 1525 and, in so doing, also may read from or write to the memory various information processed and or generated pursuant to execution of the instructions.

The example computer system 1500 also includes an assessment module 1530. Assessment module comprises processor-executable instructions for performing any of the methods described herein to, for example, provide an indication of a flow rate, or to provide an indication of the efficacy of a procedure to disrupt nerves based on the measured values of flow rate. Processor 1520 can be used to execute the processor-executable instructions in connection with assessment module 1530.

The processor 1520 of the computer system 1500 shown in FIG. 15 also may be communicatively coupled to or control the communications interface(s) 1505 to transmit or receive various information pursuant to execution of instructions. For example, the communications interface(s) 1505 may be coupled to a wired or wireless network, bus, or other communication means and may therefore allow the computer system 1500 to transmit information to and/or receive information from other devices (e.g., other computer systems). Communication interface(s) 1505 also may be in communication with an external network 1535. In some implementations, the communications interface(s) may be configured (e.g., via various hardware components or software components) to provide a website or applications program (an App) on a handheld device as an access portal to at least some aspects of the computer system 1500. Non-limiting examples of such hand-held devices are tablets, slates, smartphones, electronic readers, or other similar hand-held electronic devices.

The output devices 1510 of the computer system 1500 shown in FIG. 15 may be provided, for example, to allow various information to be viewed or otherwise perceived in connection with execution of the instructions. The input device(s) 1515 may be provided, for example, to allow a user to make manual adjustments, make selections, enter data or various other information, or interact in any of a variety of manners with the processor during execution of the instructions.

Figures 16A, 16B:
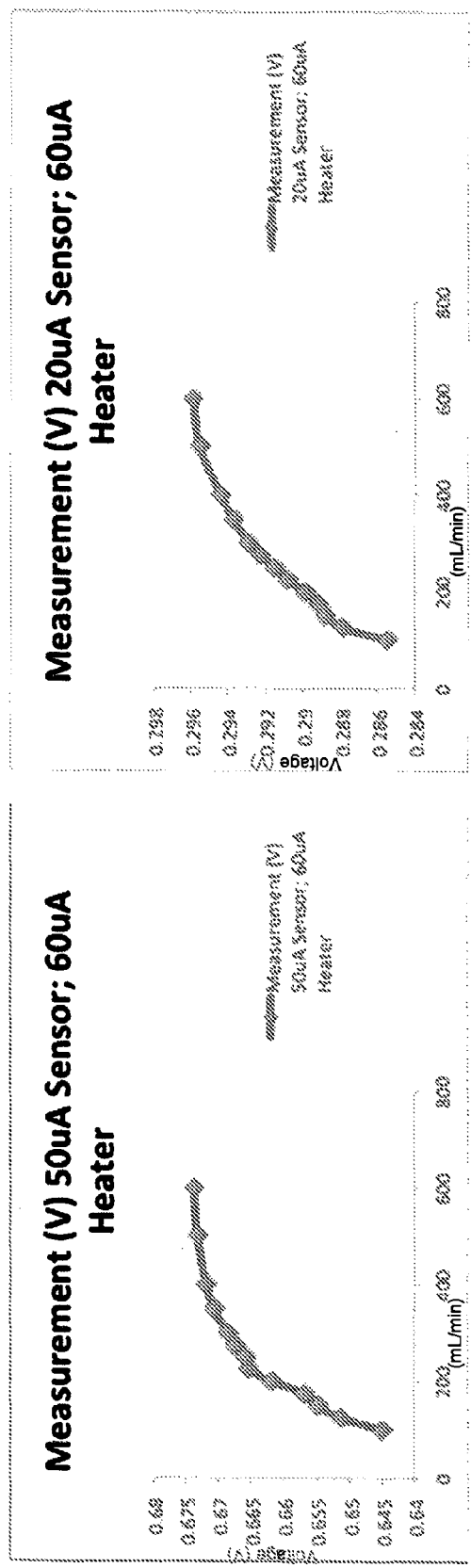
FIGS. 16A and 16B show the results of example measurement using an example device, according to the principles described herein.

FIGS. 16A and 16B show the results of example measurement using an example device according to the principles described herein. FIGS. 16A and 16B show data from flow sensor measurements over a dynamic range of flow rates (from about 100 mL/min to about 600 mL/min) for a flow sensor strategically tuned for renal hemodynamic. FIG. 16A shows measurements made for a 50 microAmps sensor. FIG. 16A shows measurements made for a 20 microAmps sensor.

Figures 17A, 17B:
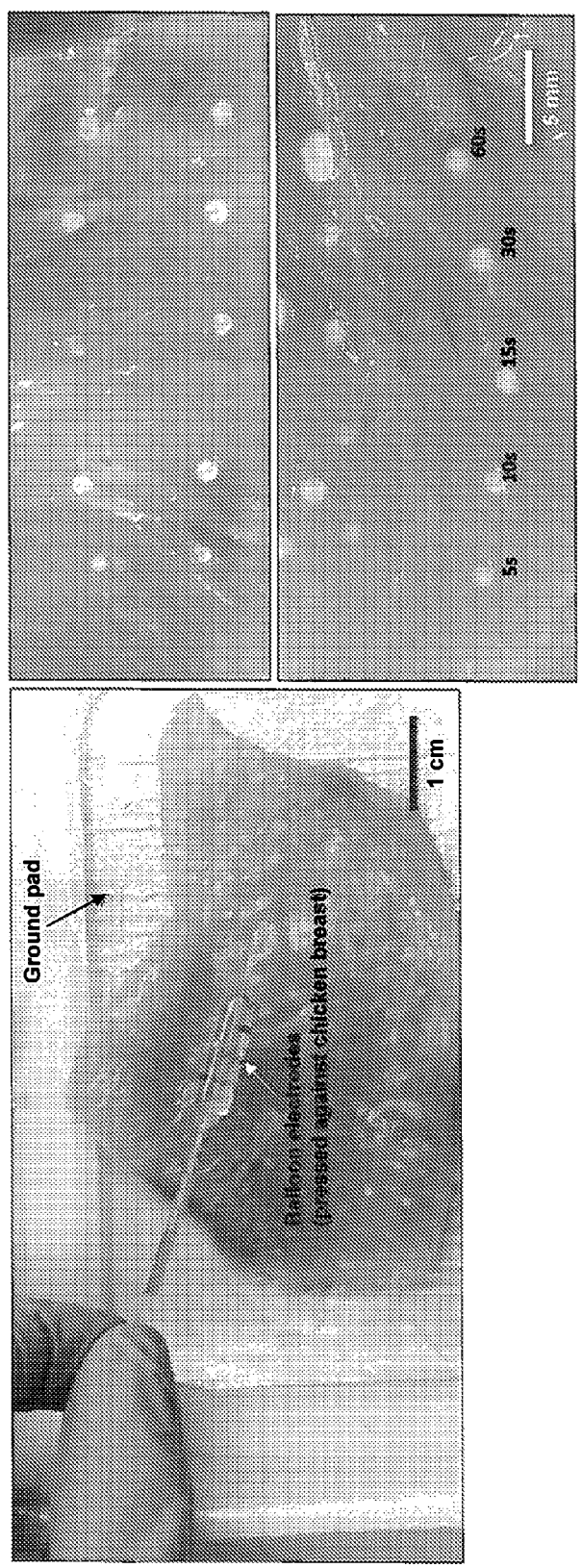
FIGS. 17A and 17B show the results of example use of an example device, according to the principles described herein

FIGS. 17A and 17B show the results of example use of an example device according to the principles described herein for use in performing an ablative procedure at about 0.2 W to about 0.3 W of power using electrodes for different exposure times (5 sec, 10 sec, 15 sec, 30 sec, 60 sec). The ablation electrodes are shown to generate lesions within about 5 seconds of contact with tissue, without charring. It is observed that a lesion is generated once the electrodes are in contact with the tissue, soft contact was sufficient to generate lesions, without excess pressure being exerted.

An non-limiting example measurement implementation is described. A system according to the principles described herein can be used to process differential measurement. If one sensor is used, the body temperature of the subject would be taken into account as well as static flow of the subject. This may require calibrations that may differ from patient to patient, leading to less accurate results or may require the physician to slow the procedure to take separate body temperature static blood flow measurements in addition to the renal artery flow measurement.

Non-limiting examples of the innovations described in this disclosure include:

a) Expediting up the clinical procedure;
b) Providing more accurate results to the end point in therapy; and
c) Reducing the amount of computation required.

In a non-limiting example, temperature sensing devices can be used in combination with a catheter to provide flow measurements. Electrical circuits can be used to provide differential measurements. Thin, stretchable, flexible and/or conformal electronics can be used to provide thin and conformal means to deploy the sensors described herein on the balloon of the catheter. The flow sensing systems, device, and methods described herein can be used for blood flow quantification and for other types of fluid flows.

In different example implementations, the change in flow can be reported to the clinician via direct values. The changes in flow can be used to show the stage, the progress, or the degree of success, of a procedure being performed, such as but not limited to an ablation procedure, for example, by indicating on a console or display device the procedure status. For example, a change in the flow rate above a defined value or threshold, can be used to signal or trigger an action. In an example, the action can be the turning on of an indicator on the catheter device, or the display of an icon, numeric value or chart on a display. In an example, the signal or trigger of the action can be used to provide the indication of the stage, the progress, or the degree of success of a procedure.

According to the example systems, methods and devices herein, sensing technology onboard catheters are described that employ thin, conformal arrays of sensors that can deform with the curvilinear structure of various balloon and spiral-shaped catheters. The ability to integrate conformal sensors along with silicon-based electronics on spiral-shaped extrusions and balloons facilitates, for the first time, ways to integrate multimodal sensory elements, micro-light emitting diodes (μLEDs) and integrated circuit building blocks (i.e. amplifiers and logic gates) onboard catheters, thereby optimizing sensing while at the same time, not impacting the mechanical properties.

Figure 18C:
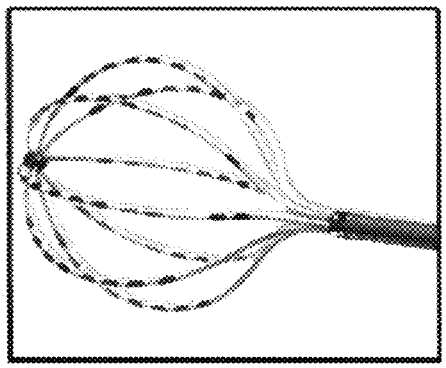
FIGS. 18A-18G illustrates examples of multi-electrode and balloon catheter devices, according to the principles described herein.
Figure 18B:
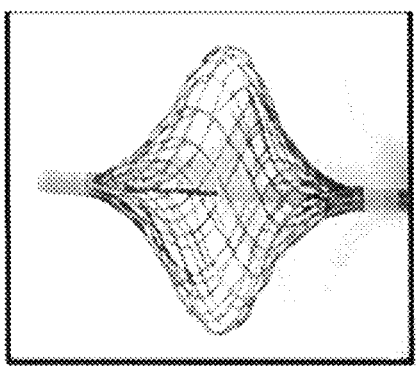
Figure 18A:
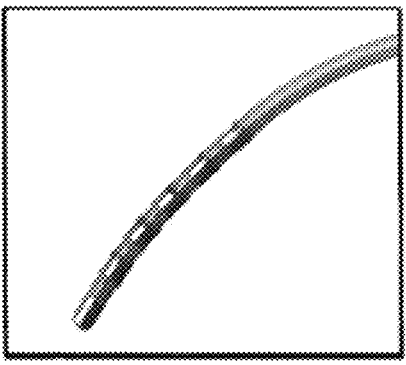
Figure 18E:
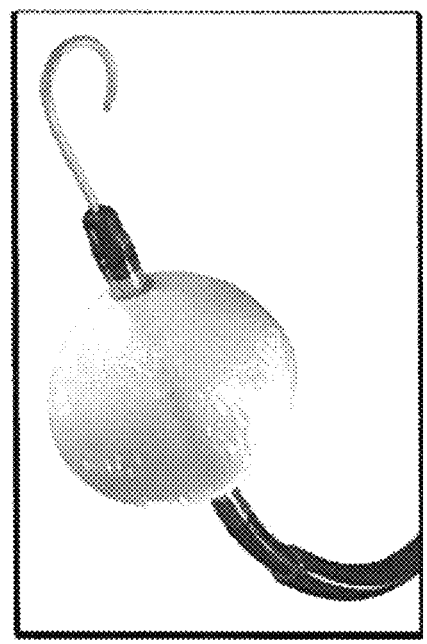
Figure 18D:
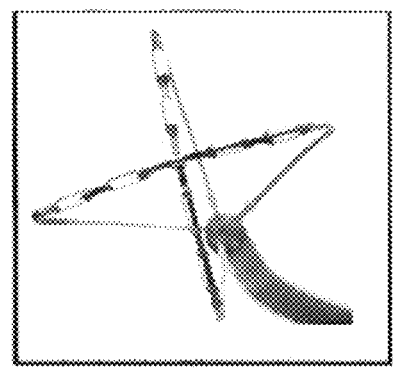
Figure 18G:
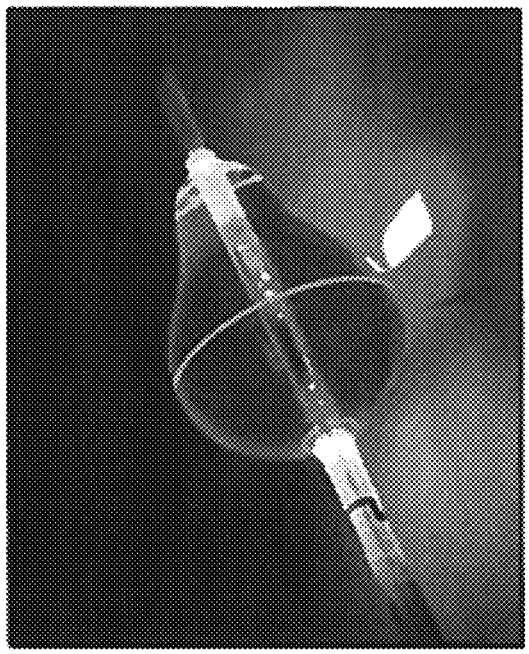
Figure 18F:
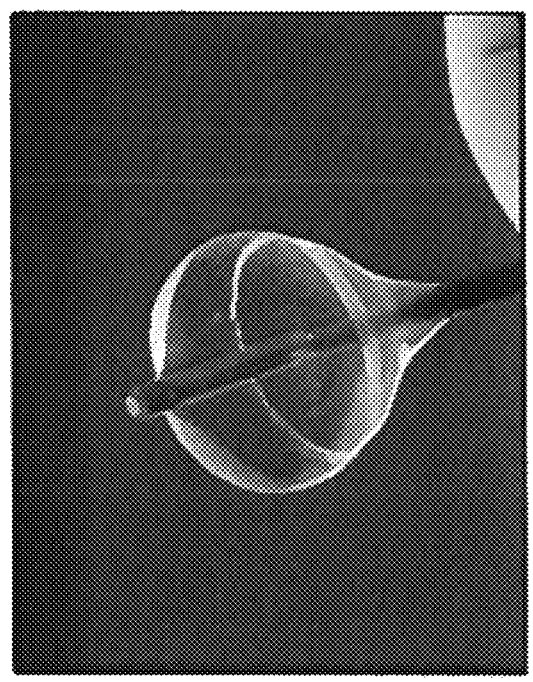

FIGS. 18A-18G illustrates examples of multi-electrode and balloon catheter devices, according to the principles described herein. FIGS. 18A-18G illustrates examples of multi-sensing element (including multielectrode) devices and catheter devices. The devices in FIGS. 18A-18D include passive wires with polyimide-based encapsulation. The wires are exposed in select areas, thus forming electrode contacts. The electrode array can include, for example, 64 electrodes. FIGS. 18E-18G show the balloon-based ablation catheters that can be used to apply cryo-, laser-, and high intensity ultrasound-forms of therapy, respectively, when deployed proximate to tissue. Any system according to the principles described herein can be implemented using any of the catheters shown in FIGS. 18A-18G.

Other non-limiting examples of catheters that are applicable to the systems, methods, and apparatus described herein include Mallecot catheters, spiral coil catheter, mesh catheters, single-Rod catheters, compliant balloon-based catheters, non-compliant balloon-based catheters, lasso-shaped catheters, multispline catheters, dilatation balloon catheters, and angioplasty balloon catheters.

Figure 19D:
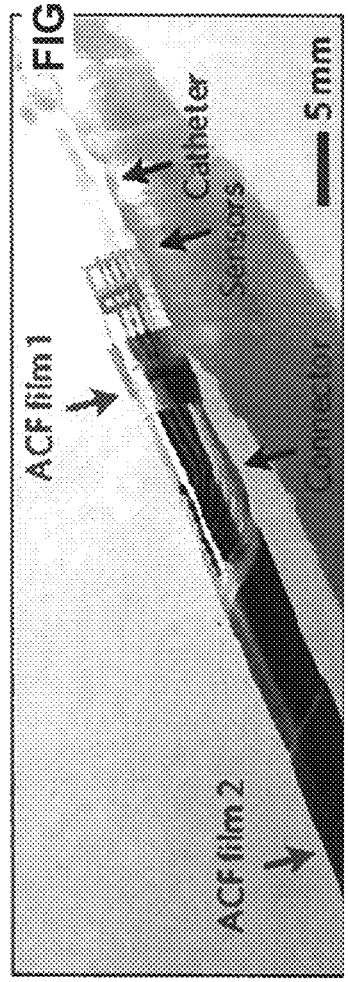
Figure 19F:
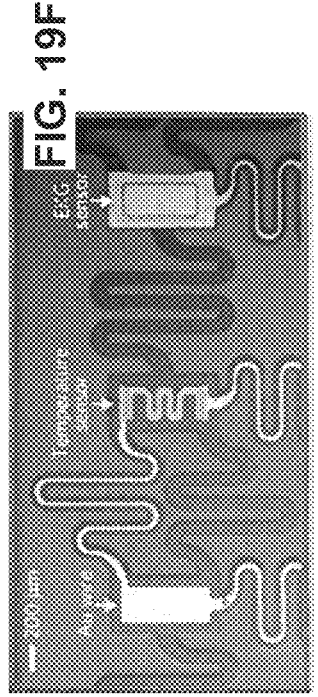
FIGS. 19E and 19F shows example forms of sensing, according to the principles described herein.
Figure 19E:
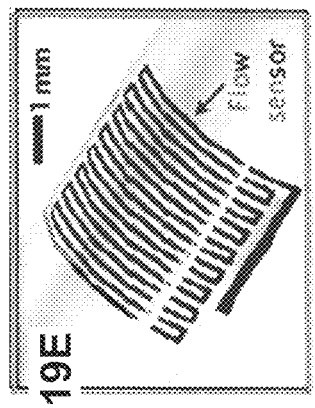

Examples of this kind of device are shown in FIGS. 19A-19D. Electrodes, flow sensors and μLEDs are able to withstand the significant mechanical strains caused by repetitive inflation and deflation cycles of the balloon by virtue of their nanomembrane form factor and the serpentine interconnect geometries, which help to absorb mechanical strains. FIGS. 19E and 19F highlight alternative forms of sensing—temperature sensors, electrodes and flow sensors on conformal substrates. The flow sensing and electrode elements are useful for RSDN catheters, because assessment of blood flow can be achieved quickly, without the need for separate diagnostic devices.

In an example, 3-omega sensor arrays are used to measure thermal conductivity and other related thermal, mechanical and material properties that relate to thermal conductivity. To measure flow, the sensors are each positioned perpendicularly to the flow direction. Such a configuration can be compatible with the design of a spiral shaped catheter system. AC current is applied across each sensor and the resulting AC voltage is measured. This measured voltage decreases monotonically as flow rate increases and increases if the blood is stagnant or slows down. Computations of measured voltages according to any of the example devices herein can be calibrated using a perfusion chamber and the flow is assumed to follow the Hagen-Poiseuille equation and its respective assumptions. Measurements using 3-omega sensor technology are versatile because they can be used to extract several other physical parameters that may be relevant to clinicians. This sensing modality can be used to serve as a viable platform for RSDN catheters.

In an example, mechanical modeling of flow sensors and electrodes during mechanical stress can be performed. Using modeling simulations, the dynamic material and mechanical properties can be characterized for conformal sensor arrays on balloon and spiral-shaped catheters that experience significant bending and twisting during operation. This includes analytical and finite element modeling of the mechanics of flex electronics affixed to balloon catheters. The strain distributions obtained through analytical and computational modeling capture, quantitatively, the nature of deformations in the electronics layers. Characterization of the effective strain and displacement distributions in the sensor islands and serpentine interconnects provide important insights into critical fracture strains and buckling phenomena. Such characterization of conformal sensors can dramatically improve the way nanomembrane flow sensors and electrodes are designed and implemented on highly deformable substrates (i.e. deflectable catheters). Furthermore, the approach holds promise for increasing the understanding of the mechanical stresses involved during catheter deployment in vivo.

Figure 20:
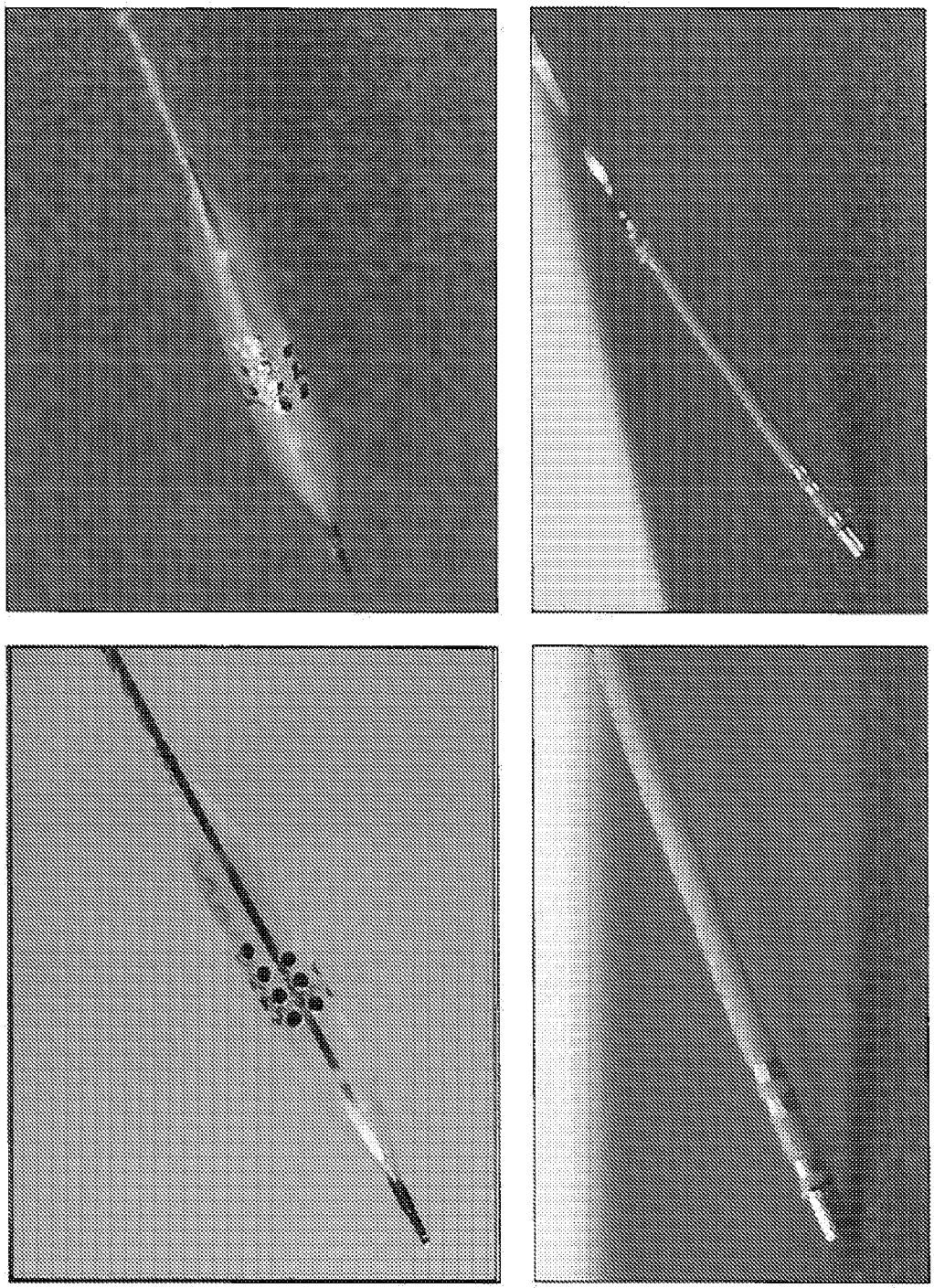
FIG. 20 shows a non-limiting example of flow sensors on catheters, according to the principles described herein.

FIG. 20 shows non-limiting examples of flow sensors on rod-shaped catheters that include "clover-shaped" flow sensors. The metal rectangles are electrodes on the catheter. In some of the example catheters of FIG. 20, the flow sensors include angioplasty balloons with ablation electrodes (the circular pads). In the novel example systems herein, the clover flow sensors are combined with the balloon electrodes on a single device.

According to the systems and methods described herein, ablation electrodes can be embedded on angioplasty balloon along with the clover-shaped flow sensors on the proximal and distal sides of the balloon on the catheter extrusion. According to the novel systems and methods herein, a multifunctional balloon catheter that has (i) array of electrodes is coupled with (ii) flow sensors embedded on the catheter's shaft proximate to the balloon. In some examples, the balloon catheter may include other sensors on the balloon, such as but not limited to LEDs, contact sensors, pressure sensors, biological activity sensors, and temperature sensors.

In an example implementation, the catheter with balloon is deployed proximate to the renal tissue (or other portion of the renal system) in a deflated state. For example, once the catheter is in the renal artery, fluid flow can be measured (including blood flow). Once captured, the balloon can be inflated and the ablation can be performed. Once the ablation is completed, or at selected points during performance of the ablation, the balloon can be deflated and flow is sensed again to see what changes are measured. In this example, an increase in flow can be used to serve as an indicator of a successful ablation procedure.

In another example implementation, the nerve can be paced and the flow can be measured pre-ablation. The ablation cycle can be performed. Once the ablation is completed, or at selected points during performance of the ablation, the nerve can be paced and the flow can be measured again (including a post-ablation measurement). If the pacing is determined to causes a change in flow, that can be used as an indicator that the nerves are still active. If the pacing does not cause a shift in flow, this can be used as an indicator that the nerves have been successfully denervated. The flow sensors coupled with ablation electrodes according to the systems and methods described herein facilitate this novel analysis and determination of clinical endpoint.

Figure 21:
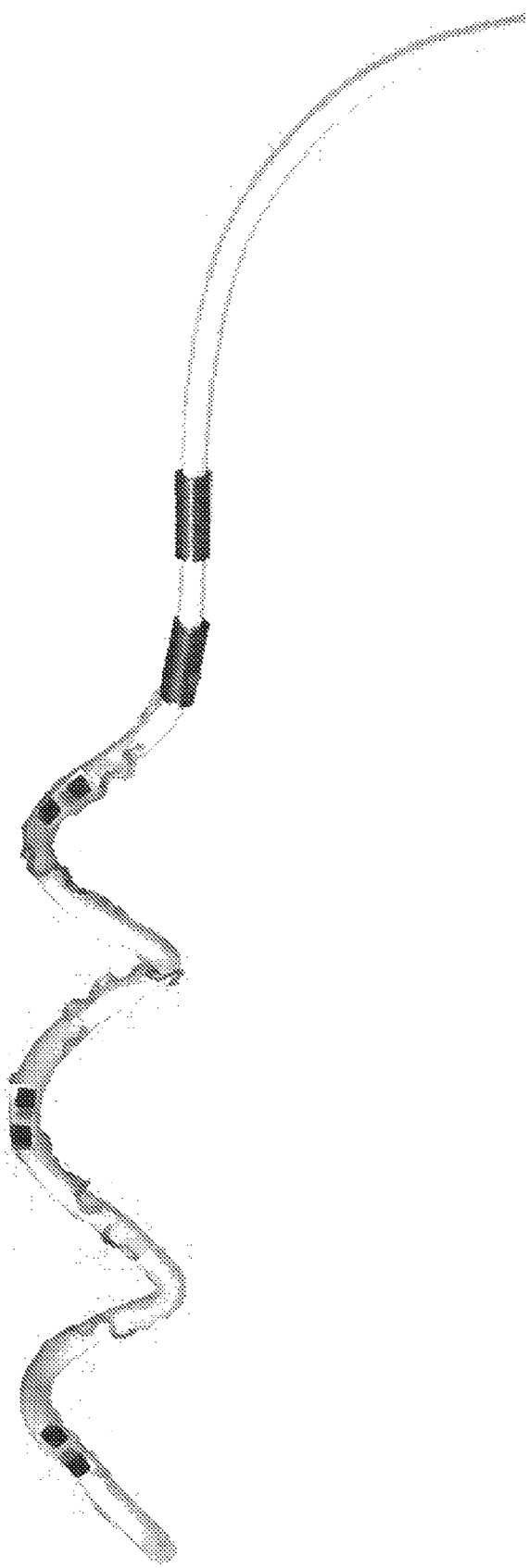
FIG. 21 shows an example of flow sensors on a spiral-shaped catheter, according to the principles described herein.
Figure 22:
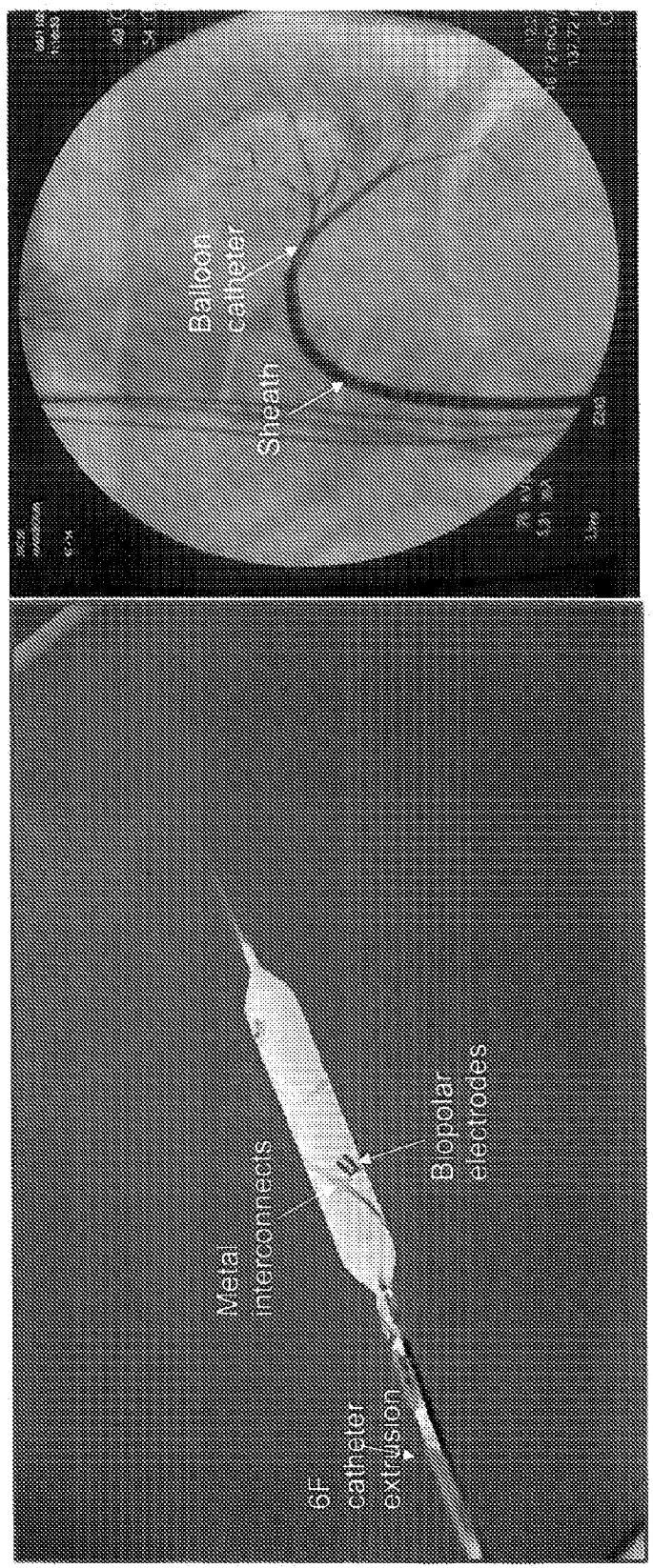
FIG. 22 shows a catheter with bipolar electrodes and metal interconnects, according to the principles described herein.

FIG. 21 shows a non-limiting example of flow sensors on a spiral-shaped catheters. FIG. 22 shows a catheter with bipolar electrodes and metal interconnects disposed on its surface.

Example design and fabrication are described for examples of 4 flow sensors, 4 pacing electrodes and 4 ablation electrodes all co-located on spiral-shaped catheters. A custom data acquisition system is implemented, and the initial functionality of the flow sensors and electrodes is tested by deploying them in flow perfusion chambers. Example combined functionalities of the flow sensors, pacing electrodes and ablation electrodes in the renal arteries of live porcine models are also described. Spiral catheters containing the sensors and electrodes are used to measure blood flow during nerve stimulation immediately pre- and post renal ablation event. A comparative analysis is conducted of a catheter system's performance, ease of use, and procedure time relative to other renal ablation devices being used in the clinical setting to gain insight into how having a clinical endpoint in RSDN helps to improve the overall procedure efficacy and safety.

Non-limiting examples of flow sensors, pacing and ablation electrodes on multifunctional spiral catheter in perfusion apparatus is described. Constrained spaces in the renal artery can reduce the number of devices that can be positioned inside. As a result, it can be challenging to deploy multiple devices in such as a confined space as in the renal arteries. Multifunctional RSDN catheters are constructed with electrodes on spiral-shaped extrusions that are small enough to conform to the renal artery to enable electrical stimuli delivery without affecting measurements. Mechanically optimized nanomembrane electrodes are incorporated with 3-omega flow sensors that interface with the limited space of the renal artery. In an example, up to 8 electrodes ($0.25 \times 0.25$ mm$^2$) and 4 ($1 \times 1$ mm$^2$) sensors are fabricated to measure renal blood flow pre- and post-ablation events. A data acquisition system (National Instruments Inc.) is implemented, coupled with an Electrical stimulator console (Medtronic Inc.) to deliver the 5-10 W of energy to pace and ablate the renal nerves. This power supply can be used to apply pacing energy. Using this new system, fundamental limits of the ablation and pacing electrodes with in vitro tissue can be characterized. In addition, a custom perfusion chamber can be built to test the flow sensing capabilities. Taken together, these new designs, microfabrication approaches and measurements using in-vitro models can provide insight into the optimal configuration of electrodes and flow sensors necessary determine changes in flow rate following renal denervation.

Non-limiting example pacing and ablation electrodes on spiral catheter and test performance in vitro are described. Ultrathin geometries impart flexibility to otherwise rigid and brittle materials. Ultrathin conformal nanomembrane sensors (~250 nm) embedded in thin polyimide and elastomeric substrates (~50-100 μm) in neutral mechanical plane layouts accommodate significant mechanical durability with radii of curvature less than about 1 mm. To achieve conformal sensors with such designs, arrays of electrodes can be formed on silicon. Lithographic processing and vertical trench wet-etching techniques yield isolated chiplets (~0.25×0.25 mm$^2$, and ~1-5 μm thick) that remain tethered to the underlying wafer through 'anchor' structures. This process can be used to yield electrodes that are referred to as 'printable', due to their ability to be removed and placed onto a target substrate with a soft, elastomeric stamp and transferred onto a spiral catheter. The attractive features of this approach include: (1) ultrathin circuit layouts for mechanical flexibility to conform to limited space in the renal artery, and (2) compatibility with other elements such as contact or flow sensors.

The utility of nanomembrane electrodes are tested be perform ablation measurements by driving RF energy (5-10 W) to show that renal nerves fibers can be ablated through arterial vessel. Histological assessment is performed of the nerves pre- and post ablation cycles to test nanomembrane electrode array performance and to see if the surface properties of the electrodes change over time (as a result of protein coating and/or electromosis phenomena). Measurements performed in the heart and on excised muscle tissue yield promising results on both pacing and ablation with this new class of nanomembrane electrodes.

A non-limiting example data acquisition system is described. Stimulation waveforms in the form of rectified triangular pulses with fixed amplitude of 10-20 V and 100-150 ms durations can be delivered through the pacing electrodes using instructions programmed into machine readable instructions. The waveform patterns are chosen strategically to induce renal nerve activity and to give rise to vasoconstriction or changes in local blood flow. The data acquisition system includes three modules to measure blood flow, induce nerve stimulation, and deliver ablation energy. The data from any of these modules can be transmitted to the assessment module to perform an assessment of efficacy as described in connection with any of the examples described herein. A National Instruments Inc. PXI-6289 (a multifunction M Series data acquisition (DAQ) system), controlled with custom machine readable instructions (including in LABVIEW™ software), controls voltages across the sensors.

Non-limiting example flow sensing, pacing and ablation using multifunctional spiral catheters in live animal models are described. Multifunctional balloon and spiral shaped catheter described in section 1 above are applied to flow sensing and ablation measurements in live animal models. Balloon catheters can be used. In an example, balloon catheters may have larger profiles that can affect flow. In a non-limiting example, to minimize effects of the catheter on blood flow, spiral-shaped catheters can be used instead of balloons. Flow can be measured upon initial deployment in the renal arteries over the course of a few minutes to determine the initial average flow rate. Once established, pacing can ensue and flow can be monitored concurrently. A 20-30% reduction in flow can be expected during this step if the renal nerves are functioning properly. Once this initial calibration is completed, the same set of procedures can be run following renal ablation cycles. It is possible that the renal blood flow may shift to a different baseline than in the initial measurement. In an example, this is not used as an indicator of successful ablation. If ablation is successful, there can be an interpretable effect that can be apparent during pacing. That is, there may be little shift in flow during pacing because the vasoconstriction properties of the nerves can be dysfunctional, which can serve as the clinical endpoint of the procedure.

In an example, an example method for determining renal denervation endpoint when blood pressure and flow are modulated with nitroglycerine is described. To determine how changes in flow can be assessed with the sensors described herein, variations in blood flow caused by nitroglycerine lead to changes in blood pressure and renal blood flow rates before and after ablation can be monitored. Systemic injections of nitroglycerine can cause shifts in blood pressure that can give rise to changes in renal blood flow. Injections of nitroglycerine also can be monitored to determine an affect on blood flow pre-pacing and again following pacing.

In an example, leakage currents and encapsulation are described. Conformal flow sensor arrays can be fabricated using a multi-layer process, which has a thin layer polyimide as the encapsulating layer. Horizontal and vertical interconnect layers are insulated using this thin layer of polyimide. In an example system, leakage currents may escape and lead to noisy recordings, bubble formation in the fluid, or sensor deterioration over time. In an example, to prevent leakage currents in these systems, additional polymeric encapsulation (UV curable polyurethanes or parylenes) can be coated over the sensors, creating an additional ~10 m encapsulating layer to withstand current leakage effects. Over the course of a few hours (the extent of RSDN procedures), leakage currents may be manageable with polyurethane, parylene and UV curable encapsulation strategies.

Data visualization and signal fidelity is described. Data acquisition systems developed for recording flow, pacing and ablation may not be provided in a single module. The visualization of the measurements recordings and stimuli application may require feedback from multiple physicians. Interpretation of the flow data in real time can be challenging. A first generation data acquisition system is described for measuring and displaying flow. In an example, the user interface can be configured to be presented on the same LABVIEW™ display as the controls for pacing and ablation, thereby providing all of the catheter control features on a single console. This system architecture may be well suited for a product development implementation.

Renal nerve stimulation is described. In some examples, the nerve pacing electrodes may lose contact with the arterial vessel wall. This variability in good contact may cause poor denervation results. To counter this effect, x-ray imaging and electrode impedance recordings can be monitored to restore proper contact with the vessel wall.

While various inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be examples and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that inventive embodiments may be practiced otherwise than as specifically described. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

The above-described embodiments of the invention may be implemented in any of numerous ways. For example, some embodiments may be implemented using hardware, software or a combination thereof. When any aspect of an embodiment is implemented at least in part in software, the software code may be executed on any suitable processor or collection of processors, whether provided in a single device or computer or distributed among multiple devices/computers.

Also, the technology described herein may be embodied as a method, of which at least one example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

All definitions, as defined and used herein, should be understood to control over dictionary definitions, definitions in documents incorporated by reference, and/or ordinary meanings of the defined terms.

The indefinite articles "a" and "an," as used herein in the specification, unless clearly indicated to the contrary, should be understood to mean "at least one."

The phrase "and/or," as used herein in the specification, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of."

As used herein in the specification, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc

What is claimed is:

1. A device, comprising:
   a catheter;
   an inflatable and/or expandable body coupled to the catheter;
   an electronic circuit disposed on the inflatable and/or expandable body, the electronic circuit comprising a plurality of components that accommodate expanding of the inflatable and/or expandable body, the plurality of components comprising:
     a plurality of electrodes, at least one electrode of the plurality of electrodes being a radiofrequency electrode configured to deliver a radiofrequency energy to a tissue proximate to the radiofrequency electrode; and
     a plurality of stretchable interconnects disposed on the inflatable and/or expandable body, wherein the plurality of stretchable interconnects electrically couples at least one of the plurality of electrodes to an external circuit;
   at least one flow sensor coupled to the catheter;
   at least one component coupled to the catheter and configured to perform an ablation procedure on a portion of a tissue proximate to the catheter; and
   an assessment module coupled to the at least one flow sensor and configured to receive data indicative of at least one flow measurement from the at least one flow sensor and provide an indication of the efficacy of the ablation procedure based on the data indicative of at least one flow measurement.

2. The device of claim 1, wherein the plurality of components further comprises a main bus, and wherein the plurality of stretchable interconnects electrically couples at least one of the plurality of electrodes to the main bus, and wherein the main bus is coupled to the external circuit.

3. The device of claim 1, wherein the tissue proximate to the catheter is a portion of a renal artery and wherein the at least one flow measurement of the at least one flow sensor provides an indication of a rate of renal blood flow.

4. The device of claim 3, wherein at least one electrode of the plurality of electrodes is a pacing electrode configured to deliver an electrical stimulation to a portion of the renal artery proximate to the pacing electrode.

5. The device of claim 4, wherein the electrical stimulation is applied to the portion of the renal artery proximate to the pacing electrode prior to performance of the ablation procedure on the portion of the renal artery proximate to the catheter.

6. The device of claim 4, wherein the electrical stimulation is applied to the portion of the renal artery proximate to the pacing electrode subsequent to performance of the ablation procedure on the portion of the renal artery proximate to the catheter.

7. The device of claim 1, wherein the tissue proximate to the catheter is a portion of a renal artery, and wherein the data indicative of at least one flow measurement comprises a change in heat output by the heating element to restore the temperature of the fluid proximate to the temperature sensor to a specified temperature.

8. The device of claim 1, wherein the inflatable and/or expandable body has a proximal end and a distal end, and the at least one flow sensor is disposed on a portion of the proximal end and/or a portion of the distal end of the inflatable and/or expandable body.

9. The device of claim 8, wherein the inflatable and/or expandable body is disposed near a distal end of the catheter.

10. The device of claim 9, wherein the catheter has a longitudinal axis, and a longitudinal axis of the distal end of the inflatable and/or expandable body coincides with the longitudinal axis of the catheter.

11. The device of claim 10, further comprising a reference flow sensor disposed on a shaft of the catheter, wherein the reference flow sensor provides an indication of a flow rate of fluid proximate to the shaft.

12. The device of claim 11, wherein the catheter further comprises a sheath, wherein the catheter is deployed through the sheath, and wherein the sheath is deployable to cover a portion of the reference flow sensor.

13. The device of claim 7, wherein the temperature sensor is a thermistor, a thermocouple, a resistance temperature detector, a junction potential temperature sensor, an integrated-circuit temperature sensor, or a semiconductor temperature sensor.

14. The device of claim 1, wherein the ablation procedure is a radiofrequency ablation, a cryo-ablation, an ultrasound ablation, a laser-light-based ablation, a drug-based ablation, an ultrasound energy ablation, an alcohol injection-based ablation, or a microwave energy ablation.

15. The device of claim 1, wherein the radiofrequency electrode is a bipolar electrode or a unipolar electrode.

16. The device of claim 1, wherein the plurality of components further comprises at least one of a light-emitting device, a contact sensor, an image detector, a mapping electrode, a pressure sensor, a biological activity sensor, and a temperature sensor.

17. The device of claim 1, wherein the inflatable and/or expandable body is a compliant balloon.

18. The device of claim 1, wherein the inflatable and/or expandable body is an expandable spiral coil, an expandable mesh, or a deployable netting.

19. The device of claim 1, further comprising:
at least four flow sensors disposed on the inflatable and/or expandable body, and wherein the plurality of components comprises at least four pacing electrodes and at least four radio frequency electrodes.

20. The device of claim 1, wherein the tissue is a portion of a tissue lumen.

21. The device of claim 1, wherein the tissue is a renal artery, a pulmonary vein, a coronary artery, or a peripheral blood vessel.

22. A method of performing a medical diagnosis and/or treatment on a tissue, the method comprising:
disposing in proximity to the tissue an apparatus comprising:
a catheter;
an inflatable and/or expandable body coupled to the catheter;
an electronic circuit disposed on the inflatable and/or expandable body, the electronic circuit comprising a plurality of components that accommodate expanding of the inflatable and/or expandable body, the plurality of components comprising:
a plurality of electrodes, at least one electrode of the plurality of electrodes is a radiofrequency electrode configured to deliver a radiofrequency energy to a tissue proximate to the radiofrequency electrode; and
a plurality of stretchable interconnects disposed on the inflatable and/or expandable body, wherein the plurality of stretchable interconnects electrically couples at least one of the plurality of electrodes to an external circuit;
at least one flow sensor disposed on a portion of the catheter, each of the at least one flow sensor comprising:
a heating element; and
a temperature sensor disposed proximate to the heating element, wherein a flow measurement of the at least one flow sensor provides an indication of a flow rate of a fluid proximate to the portion of the catheter;
at least one component coupled to the catheter and configured to perform an ablation procedure on a portion of a tissue proximate to the catheter; and
an assessment module coupled to the at least one flow sensor and configured to receive data indicative of at least one flow measurement from the at least one flow sensor and provide an indication of the efficacy of the ablation procedure based on the data indicative of at least one flow measurement;
applying the ablation procedure to the surface of the tissue proximate to the catheter; and
recording the at least one flow measurement of the at least one flow sensor.

23. The method of claim 22, further comprising the recording of the at least one flow measurement prior to and subsequent to performing the ablation procedure, and wherein the ablation procedure is a radiofrequency ablation, a cryo-ablation, an ultrasound ablation, a laser-light-based ablation, a drug-based ablation, an ultrasound energy ablation, an alcohol injection-based ablation, or a microwave energy ablation of the tissue.

24. The method of claim 22, wherein the recording of the at least one flow measurement of the at least one flow sensor is performed subsequent to the applying of the ablation procedure to the surface of the tissue proximate to the catheter.

25. The method of claim 22, wherein the recording of the at least one flow measurement of the at least one flow sensor is performed prior to the applying of the ablation procedure to the surface of the tissue proximate to the catheter.

26. The method of claim 25, further comprising:
the recording of the at least one flow measurement of the at least one flow sensor subsequent to the applying of the ablation procedure to the surface of the tissue proximate to the catheter; and
comparing data indicative of the at least one flow measurement prior to the applying of the ablation procedure to data indicative of the at least one flow measurement subsequent to the applying of the ablation procedure to provide the indication of the efficacy of the ablation procedure.

27. The method of claim 26, wherein an indication of an increase in the flow rate of the fluid provides an indication of the efficacy of the applying of the ablation procedure to the surface of the tissue.

28. The method of claim 22, wherein the catheter further comprises a pacing electrode configured to deliver an electrical stimulation to a portion of a tissue proximate to the pacing electrode.

29. The method of claim 28, further comprising delivering the electrical stimulation to the portion of the tissue proximate to the pacing electrode prior to a recording of at least one temperature measurement of the temperature sensor.

30. The method of claim 22, wherein the tissue is a left renal artery, a right renal artery, and/or a carotid body.

31. The method of claim 30, wherein an indication of an increase in the flow rate of the fluid provides an indication of the efficacy of the applying of the ablation procedure to the surface of the left renal artery, the right renal artery, and/or the carotid body.

32. The method of claim 31, wherein the applying of the ablation procedure to the surface of the renal artery causes an ablation of a nerve proximate to the surface of the renal artery.

33. A catheter device for performing a procedure on tissue of a renal artery, comprising:
an inflatable and/or expandable body disposed near a distal end of the catheter device;
an electronic circuit disposed on the inflatable and/or expandable body, the electronic circuit comprising a plurality of components that accommodate expanding of the inflatable and/or expandable body, the plurality of components comprising:
a plurality of electrodes, at least one electrode of the plurality of electrodes is a radiofrequency electrode configured to deliver a radiofrequency energy to a surface proximate to the radiofrequency electrode to perform an ablation procedure on a portion of the tissue of the renal artery; and
a plurality of stretchable interconnects disposed on the surface of the inflatable and/or expandable body, wherein the plurality of stretchable interconnects electrically couples at least one of the plurality of electrodes to an external circuit; and
at least one flow sensor disposed on the inflatable and/or expandable body, each of the at least one flow sensor comprising:
a heating element configured to heat an area proximate to the inflatable and/or expandable body; and
a temperature sensor disposed proximate to the heating element, wherein measurement of the temperature sensor provides an indication of a flow rate of blood in the renal artery proximate to the inflatable and/or expandable body.

34. The catheter device of claim 33, wherein the at least one component comprises at least one radiofrequency electrode disposed on the inflatable and/or expandable body and configured to deliver a radiofrequency energy to the portion of the tissue of the renal artery.

35. The catheter device of claim 33, wherein the at least one component comprises a cauterizing element or a cryoablation component.

36. The catheter device of claim 33, wherein the plurality of components further comprises a main bus, and wherein the plurality of stretchable interconnects electrically couples at least one of the plurality of electrodes to the main bus, and wherein the main bus is coupled to the external circuit.

37. The catheter device of claim 33, further comprising at least one pacing electrode disposed on the inflatable and/or expandable body and configured to deliver an electrical stimulation to a portion of the tissue of the renal artery proximate to the pacing electrode.

38. The catheter device of claim 37, wherein the electrical stimulation is applied to the portion of the renal artery prior to performing the ablation procedure on the portion of the tissue of the renal artery.

39. The catheter device of claim 37, wherein the electrical stimulation is applied to the portion of the renal artery subsequent to performing the ablation procedure on the portion of the tissue of the renal artery.

40. The catheter device of claim 33, further comprising at least one of a light-emitting device, a contact sensor, an image detector, a mapping electrode, a pressure sensor, a biological activity sensors, and a temperature sensor, disposed on the inflatable and/or expandable body.

41. The catheter device of claim 33, wherein the inflatable and/or expandable body is a balloon.

42. The catheter device of claim 33, wherein the inflatable and/or expandable body is an expandable spiral coil, an expandable mesh, or a deployable netting.

* * * * *